(12) United States Patent
Walzman

(10) Patent No.: US 12,390,321 B2
(45) Date of Patent: Aug. 19, 2025

(54) CAPED STENT

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 1035 days.

(21) Appl. No.: 17/200,412

(22) Filed: Mar. 12, 2021

(65) Prior Publication Data

US 2021/0196447 A1 Jul. 1, 2021

Related U.S. Application Data

(63) Continuation of application No. 17/156,743, filed on Jan. 25, 2021, which is a continuation-in-part of application No. 16/214,130, filed on Dec. 9, 2018, now Pat. No. 11,007,048.

(51) Int. Cl.
*A61F 2/07* (2013.01)
*A61F 2/00* (2006.01)
*A61F 2/852* (2013.01)
*A61L 31/14* (2006.01)

(52) U.S. Cl.
CPC .............. *A61F 2/07* (2013.01); *A61F 2/0077* (2013.01); *A61F 2/852* (2013.01); *A61F 2210/0076* (2013.01); *A61L 31/145* (2013.01)

(58) Field of Classification Search
CPC .... A61F 2/95; A61F 2/82; A61F 2/852; A61F 2002/828; A61F 2/07–2002/007
See application file for complete search history.

(56) References Cited

U.S. PATENT DOCUMENTS

| | | | |
|---|---|---|---|
| 5,330,500 A | 7/1994 | Song | |
| 5,645,558 A | 7/1997 | Horton | |
| 6,379,382 B1 * | 4/2002 | Yang | A61L 31/12 623/1.42 |
| 6,428,569 B1 | 8/2002 | Brown | |
| 6,635,082 B1 | 10/2003 | Hossainy | |
| 7,118,592 B1 | 10/2006 | Dang et al. | |
| 8,343,204 B2 * | 1/2013 | Osborne | A61F 2/07 623/1.13 |
| 8,398,701 B2 | 3/2013 | Berez | |
| 9,775,730 B1 | 10/2017 | Walzman | |
| 10,039,655 B2 | 8/2018 | Pung et al. | |

(Continued)

FOREIGN PATENT DOCUMENTS

WO WO-9853761 A1 * 12/1998 ............... A61F 2/07
WO WO 2005/112823 A1 12/2005

OTHER PUBLICATIONS

Chun Fang, et al., Using a covered stent for large cerebral aneurysms treated with stent-assisted coiling (Interv Neuroradiol. Jun. 2015; 21(3):317-324).

(Continued)

*Primary Examiner* — Christopher D. Prone
(74) *Attorney, Agent, or Firm* — Neil D. Gershon

(57) ABSTRACT

An intravascular stent having a stent body and at least one cover overlying the stent body to cover the first portion of the stent body. The cover has a first region attached to the stent body and a second region unattached to the stent body. Multiple covers can be attached to the stent body in overlapping arrangement, each cover having a free unattached end. The free ends reduce the overall stiffness of the stent.

20 Claims, 21 Drawing Sheets

(56) References Cited

U.S. PATENT DOCUMENTS

| | | |
|---|---|---|
| 10,173,029 B2 * | 1/2019 | Webster ............ A61M 25/0041 |
| 10,327,790 B2 | 6/2019 | Garrison |
| 2001/0049554 A1 | 12/2001 | Ruiz |
| 2002/0121472 A1 | 9/2002 | Garner |
| 2003/0055452 A1 | 3/2003 | Joergensen |
| 2005/0027345 A1 | 2/2005 | Horan |
| 2005/0110214 A1 | 5/2005 | Shank et al. |
| 2007/0219619 A1 | 9/2007 | Dieck et al. |
| 2008/0281394 A1 | 11/2008 | Jones |
| 2009/0143853 A1 | 6/2009 | Morris et al. |
| 2012/0259404 A1 * | 10/2012 | Tieu ........................ A61F 2/852 623/1.15 |
| 2012/0310138 A1 | 12/2012 | Behan |
| 2012/0316632 A1 | 12/2012 | Gao |
| 2014/0025151 A1 | 1/2014 | Gao |
| 2019/0151072 A1 | 5/2019 | Walzman |
| 2020/0323620 A1 | 10/2020 | Walzman |

OTHER PUBLICATIONS

Shogo Nishi, et al., Treatment of rabbit carotid aneurysms by hybrid stents (microporous thin polyurethane-covered stents): Preservation of side-branches (J Biomater Appl. 2014).

PCT/US2022/012083 International Search Report and Written Opinion (Mar. 30, 2022).

European Search Report EP22742991 Dated: Nov. 22, 2024.

* cited by examiner

CAPED STENT

CROSS-REFERENCE(S)

This application is a continuation of application Ser. No. 17/156,743, filed Jan. 25, 2021, which is a continuation in part of application Ser. No. 16/214,130, filed Dec. 9, 2018, now U.S. Pat. No. 11,007,048. The entire contents of each of these applications are incorporated herein by reference.

FIELD OF THE INVENTION

The present disclosure relates to endovascular devices used to treat aneurysms and fistulas within unhealthy blood vessels, and more particularly, to covered stents positionable within blood vessels.

BACKGROUND OF THE INVENTION

The prior art teaches the use of a number of devices to treat aneurysms. A common blood vessel difficulty is the persistent blood flow in the aneurysm sac extrinsic to the endograft. In fact, this is the most common complication after endovascular aneurysm repair (EVAR). Such endoleaks are ameliorated by a number of means. For example, Walzman application Ser. No. 15/732,147 and Ser. No. 15/732,365 (Publication No. 2018-0153554) teach the use of hydrogel to prevent endoleaks.

The prior art also teaches endovascular coiling as a minimally invasive technique performed to prevent blood from flowing into some saccular aneurysms. This treatment results in the coil inducing embolization (clotting) of the aneurysm, which prevents blood from flowing into the aneurysm, which in turn, prevents rupture and for intracranial aneurysms subsequent subarachnoid hemorrhage. Endovascular coiling, however, may result in procedural complications including thromboembolism, cerebral embolization, aneurysm perforation, parent artery occlusion, coil migration, arterial dissection, and others. The prior art also teaches stent-assisted coiling. The stent-assisted coiling also has some of the same shortcomings related to stent placement and placing a stent in the parent artery and requires prolonged use of anti-platelet agents to reduce the risk of thrombosis-based stenosis within the stent.

Some aneurysms and fistulas are ideally treated with covered stents, which can most directly cover the hole of the fistula or the neck of the aneurysm and reconstruct the vessel wall, immediately redirecting blood flow into the normal path of the parent vessel. However, there are currently no covered stents that are effective in the neurovascular or in severely tortuous anatomy in other parts of the body, including for example splenic artery aneurysms and pulmonary arteriovenous fistulas.

A potentially significant use of covered neuro-stents is for the treatment of fistulas, particularly for carotid cavernous fistula (CCF) which is an abnormal communication between the cavernous sinus and the carotid arterial system.

Other treatment of aneurysms includes surgical clipping of an intracranial aneurysm, which involves the application of a clip across the neck of the aneurysm. This treatment has several shortcomings including that it requires an open operation and physical manipulation of the brain. Sometimes surgical bypass is considered as well, but typically is associated with even higher rates of morbidity and mortality.

Additionally, the prior art teaches the use of flow diversion devices to divert flow away from the aneurysm by placing a mesh stent or a structure similar to a stent, on the aneurysm neck along the parent artery. The use of these devices allows for thrombus formation inside the aneurysm. However, increased technical complications can develop following the deployment of flow diverters. Additionally, because they do not completely block flow, they are not effective in the treatment of most fistulas and ruptured vessels. Similarly, there is currently no effective vessel-sparing treatment of an iatrogenic rupture of an intracranial artery. Current treatment requires closing the ruptured artery with coils and/or liquid embolics to stop the bleeding, usually with significant resulting morbidity from ischemic injury to that arterial territory. Furthermore, when treating aneurysms with these devices, the aneurysm thromboses over time, so there is a lag period, and is not immediately cured. This leaves the patient at risk of aneurysmal rupture during the lag period. This can be especially problematic when treating ruptured aneurysms, which have high short-term re-rupture rates.

A need exists for an endovascular device capable of endovascular intervention for immediate cure of select intravascular aneurysms or fistulas, while ameliorating the difficulties and shortcomings associated with the currently available technologies. More particularly, a need exists for a covered stent which allows the stent freedom of motion and bending without kinking around tight bends in tortuous anatomy.

Most covered stents involve producing a cylinder of a stent "skeleton" or "frame" out of semi-rigid materials such as metal alloys, and then attaching an impermeable "cover" to the frame. The prior art teaches such attachments are diffuse and located throughout the covering of the stent, along fixed intervals of the covering and frame, and consequently significantly limit flexibility of the device. The need exists for a stent capable of safe and effective delivery and deployment into tortuous vessels to effectively divert blood flow away from an aneurysm, fistula, or ruptured vessel while allowing blood to flow to healthy tissue distal to the targeted treatment area and still resulting in blood stasis and thrombus formation inside the aneurysm or fistula. Thus, a need exists for a covered neuro stent as well as a covered stent which is capable of use in other tortuous anatomy outside of the brain.

SUMMARY OF THE INVENTION

The present invention overcomes the problems and deficiencies of the prior art. The present invention provides a covered stent device capable of safe and effective delivery and deployment into tortuous vessels to effectively divert blood flow away from an aneurysm, fistula, or ruptured vessel while allowing blood to flow to healthy tissue distal to the targeted treatment area and still resulting in blood stasis and thrombus formation inside the aneurysm or fistula, and/or repair and subsequent healing of the damaged vessel. The covered stents of the present invention can be utilized as a neuro stent as well as a used in other tortuous anatomy outside of the brain. These devices can be used in anatomy that is not tortuous as well.

The present invention achieves the foregoing by providing a stent with a free-floating cover. The free-floating cover is designed to optimize insertion in tortuous anatomy as the stent bends and curves during insertion through the vasculature. In some embodiments, this is achieved via a single circumferential attachment point of the cover at one end (which can be as small as about 0.1 mm for example). In some embodiments, a plurality of covers are provided and can be arranged in overlapping arrangements such as in shingle-like fashion described in detail below. The cover configuration and attachment minimizes stiffness of the device and allows for bending of the stent without kinking which could otherwise occur. Thus, as noted above, its sufficient flexibility enables its use as a covered stent for neuro applications as well as in other tortuous anatomy outside of brain.

As can be appreciated from the discussion of the various embodiments below, the stent can have a single cover or can have multiple covers at various locations and arrangements.

In some embodiments, the covers are arranged as overlapping geometric shingles attached to the stent (frame) on only one side, comprising less than 70% of the length of said shingles, with the shingle optionally attached only along a limited segment of the circumference and/or longitudinal surface of the frame. Additional overlapping shingles and their independent attachments can extend over a covered segment and uncovered segment of the stent, resulting in complete coverage of said segment(s) of the stent. Partial coverage of the stent frame with the overlapping, e.g., shingled covers, can be provided in other embodiments, with the covers together covering a majority, or alternatively, a minority, of the length of the frame. Some embodiments may also have more than one covered region.

The covered stents of the present invention can optionally be deployed under flow arrest, via pharmacologic means, or via delivery through a balloon guide catheter with temporary balloon inflation or other means, to minimize the possibility of blood flow folding or bunching the cover, e.g., fabric, as it is unsheathed. Furthermore, if a portion of the stent cover is not well apposed to a vessel wall, as can occur when it is overlapping a large fistula, a second similar covered stent can be placed inside the first covered stent, and the frame of the first covered stent will help secure the cover(s) of the second covered stent. Similarly, a different covered stent can be used as the initial outer stent, provided such outer stent has small enough interstices that the cover(s) of the second inner stent cannot herniate through those interstices.

The stent covers of the present invention can fully encircle, or, in alternate embodiments, partially encircle, a given segment of the stent (frame) such that the stent is covered only along a portion of its circumference while being uncovered at a different circumferential side/portion of the same segment. This can sometimes allow preservation of the origin of a branch vessel that might arise from the parent vessel along the same segment of said parent vessel, for example, opposite to a fistula or the neck of an aneurysm.

In accordance with one aspect of the present invention, an intravascular stent is provided comprising a) a stent body having a longitudinal axis, a first portion, a second portion and a plurality of openings; b) a first cover overlying the stent body to cover the first portion of the stent body and extending longitudinally over the first portion, the first cover having a first region and an unattached region, the unattached region having a free end, the first cover attached to the stent body at the first region; and c) a second cover overlying the stent body to cover the second portion of the stent body and extending longitudinally over the second portion, the second cover having a first region, a second region and an unattached region having a free end. The first cover overlaps the first region of the second cover and a portion of the unattached region of the second cover is not overlapped by the first cover.

In some embodiments, the first cover overlaps the second cover such that a majority of the second cover is not overlapped by the first cover. In other embodiments, the first cover overlaps the second cover such that a majority of the second cover is overlapped by the first cover.

In some embodiments, the first cover and/or the second cover are attached to an inner wall of the stent body; in other embodiments, the first cover and/or the second cover are attached to an outer wall of the stent body.

The stent body (skeleton/frame) may have a single layer or two or more layers welded together at one or more points. The stent body may be woven, or braided, or laser cut, or combinations of these—either varying along its length or two or more different frame types welded together at one or more points. The skeleton/frame can me made of one or more metals, metal alloys, or other suitable non-metallic materials.

In some embodiments, the stent is inserted into a body of a patient with the first and second stent covers attached to the stent body. That is, the covers are attached in the manufacturing process.

In some embodiments, the first and second covers are attached to an outer wall of the stent body and a second stent body is positioned over the first and second covers. This can sometimes be accomplished in vivo by first deploying the second stent body, and subsequently deploying the first stent with the attached stent covers within the confines of the second stent, thereby allowing the free-ends of the covers e.g., the shingled free ends, to be pinned between the two stent skeletons, minimizing the chance of an endoleak between overlapping covers. In other embodiments, the two stent bodies are inserted together.

In some embodiments, multiple stents each have multiple covers e.g., shingles, and are placed in vivo inside each other in a telescoping fashion to further minimize the risk of leaks through or around the covers. In some embodiments there may also be an additional substance, including but not limited to hydrogel, that coats some or all of the skeleton frame and/or the covers, which can swell in vivo and further minimize the chance of leaks between covers, e.g., shingles, and/or between the stent or stents and the vessel wall.

In some embodiments, the first and second covers extend around a full 360 degrees of the stent body; in other embodiments, the first and second covers extend around less than a full 360 degrees of the stent body. In some embodiments, the first and second covers together cover less than an entire length of the stent body.

In some embodiments the covers are cylindrically shaped; in other embodiments they are semi-cylindrical shaped; in other embodiments they are substantially triangular shaped. Other configurations and geometric shapes are also contemplated, such as like scales on a fish.

In some embodiments, the first cover and second cover are each attached to the stent body at an attachment site, and the first and second covers are expandable independent of the frame except at the attachment site.

In some embodiments, a third cover is provided overlying the stent body to cover a third portion of the stent body and extending longitudinally over the third portion, the second cover overlapping a portion of the third cover so the first, second and third covers form a shingle-like arrangement. Additional covers are also contemplated.

In accordance with another aspect of the present invention, an intravascular stent is provided comprising a) a stent body having a longitudinal axis and a plurality of openings; and b) a first cover overlying the stent body to cover a first segment of the stent body and extending longitudinally over the first segment of the stent body, the first segment having a first region and a second region. Upon bending of the stent body, a portion of the first cover moves axially with respect to the stent body so a length of the stent body covered by the first cover may be reduced along the outer curve, as the stent body typically elongates along the outer curve and the cover length remains constant. A length of the stent covers relative to the stent body may increase along the inner curve, as the stent body typically shortens along an inner curve.

In some embodiments, a second cover overlying the stent body is provided to cover a second segment of the stent body, said second segment having a first region and a second region and upon bending of the stent body, a portion of the second cover moves axially with respect to the stent body.

In some embodiments, one end of the stent has no covering. In some embodiments, both the proximal and distal end of the stent have no coverings. Similarly, branched stents are contemplated as well, with both covered and uncovered ends in various embodiments. In some embodiments, various configurations of multiple similar and/or dissimilar stents may also be used. In some embodiments, the stent may be covered at one or more ends and have one or more uncovered segments elsewhere along a length as well.

In some embodiments, upon bending of the stent body, a portion of the cover moves with respect to the stent body. In some embodiments, upon bending of the stent body, a portion of the stent body moves relative to the cover. In some embodiments, upon bending of the stent body, a portion of the stent body moves relative to the one or more covers. In some embodiments, the first cover overlaps an attachment region of the second cover without overlapping the free end of the second cover.

In some embodiments, the first cover and second cover are each attached to the frame, each at an attachment site, which may be separate or the same for both covers, and the first and second covers are expandable independent of the frame except at the attachment site. The attachment site or sites may be a single point, a line, another shape, a circumference of the frame or part of a circumference of the frame. In preferred embodiments, each cover has its own independent attachment site. In some embodiments, the first cover overlaps a partial portion of the second cover such that a majority of the second cover is not overlapped by the first cover. In other embodiments, a majority of the second cover is overlapped by the first cover.

In some embodiments, the first and second stent covers are attached to the stent body prior to insertion of the stent and placement of the stent within the vessel.

In some embodiments one or more covers are inside the frame. In some embodiments, one of more covers are on the outside of the frame. In some embodiments, one or more covers are inside the frame and one of more covers are on the outside of the frame. In some embodiments, one or more covers are in between layers of the frame. In some embodiments, one or more covers are inside the frame and one of more covers are on the outside of the frame and/or one or more covers are in between layers of the frame.

In accordance with another aspect of the present invention an intravascular stent is provided comprising a stent body having a longitudinal axis, a first portion, a second portion and a plurality of openings. A first cover is arranged to cover an axial segment of the stent body. The first cover has an attachment end attached to the stent body and an opposing free end which are movable with respect to the stent body to reduce a stiffness of the stent body. That is, the cover allows for more flexibility of the stent and less tendency to kink since they are attached only at one end.

In some embodiments, a second cover is provided having an attached end and an opposing free and end movable with respect to the stent body to reduce stiffness.

In some embodiments, each of the first and second covers combined extend over less than an entire length of the stent body. Alternatively, they extend the entire length. Alternatively, they can extend beyond the entire length.

In accordance with another aspect of the present invention, a method of preventing an endoleak in a vessel of a patient is provided comprising deploying a first stent across an opening in a vessel and subsequently inserting a second stent having a frame and a first cover within the first stent such that the first cover extends across the opening in the vessel. The first cover has a first end attached to the frame and a second free end unattached to the frame. Insertion of the second stent within the first stent pins the first cover between the first and second stents. The opening in the vessel could be for example an opening at a fistula or at a neck of an aneurysm.

In some embodiments, the second stent has a second cover having an attached end and a free end, the free end of the first cover overlying the attached end of the second cover, and the free end of the first cover pinned against the second cover to limit flow of blood between the first and second covers.

In some embodiments, the first stent is composed of a woven material and/or the second stent is composed of a non-woven material, which in some embodiments can be metallic or a polymeric material. The first and/or second stent can be balloon expandable or self-expanding. In some embodiments, the first and second stents have different porosities. In some embodiments, the second stent has a porosity of greater than 80%.

In some embodiments, at least a part of the stent body/frame and/or the cover (or multiple covers) has adhered hydrogel to help prevent endoleaks.

In accordance with another aspect of the present invention, a method of delivering a stent within a vessel of a patient is provided comprising:

a) inserting a delivery member into the vessel, the delivery member containing a stent having a frame and a first cover overlying a first portion of the frame to cover the first portion of the frame and extending longitudinally over the first portion, the first cover having a first region and an unattached region, the unattached region having a free end, the first cover attached to the frame at the first region; and b) exposing a first section of the stent from the delivery member such that the first section expands into contact with a wall of the vessel, the first region of the first cover being pinned against the wall of the vessel while the free end of the first cover remains spaced from the vessel wall as a second section of the stent is contained within the delivery member.

In some embodiments, the stent has a second cover overlying a second portion of the frame to cover the second portion of the frame and extending longitudinally over the second portion, the second cover having an attached region and an unattached region, the unattached region of the second cover having a free end, and the first cover overlying the attached region of the second cover. In some embodiments, during exposing the first portion of the stent, at least a part of the second cover is contained within the delivery member.

In accordance with another aspect of the present invention, an intravascular stent is provided positionable within a vessel of a patient comprising a) an outer layer composed of a woven material; and b) an inner layer positioned within the outer layer, the inner layer composed of an expandable material and movable from a collapsed condition to an expanded condition to facilitate expansion of the outer layer within the vessel.

In accordance with another aspect of the present invention, an intravascular stent is provided positionable within a vessel of a patient comprising a) an outer layer composed of a woven material; and b) an inner layer positioned within the outer layer, the inner layer composed of an expandable material and movable from a collapsed condition to an expanded condition to facilitate expansion of the outer layer within the vessel.

The expanding material can be self-expanding or balloon or mechanically expandable.

In some embodiments, the inner layer and outer layer have different porosities. In some embodiments, the inner layer has a porosity greater than the porosity of the outer layer. In some embodiments, the porosity of the inner layer is between about 70% and about 99.9%. In preferred embodiments the porosity could be greater than 80%. In some embodiments, the porosity range of the outer stent could be between 0% to about 80%, and in preferred embodiments about 75% porosity or less.

In accordance with another aspect of the present invention, an intravascular stent is provided having an outer layer of a first porosity and a second layer of a second porosity different than the first porosity.

In some embodiments, the outer layer has a length equal to the length of the inner layer. In other embodiments, the outer layer has a length less than a length of the inner layer. In other embodiments, the outer layer has a length greater than a length of the inner layer.

In some embodiments, one or more covers are attached to an outer wall of the inner layer and/or are attached to an inner wall of the inner layer and/or are attached to an outer wall of the outer layer and/or are attached to an inner wall of the outer layer. In some embodiments, the covers have and attached region and an unattached region having a free end. The covers can be arranged in a non-overlapping or an overlapping e.g., shingle-like, arrangement.

In some embodiments, the inner layer is inserted into the outer layer after the outer layer is positioned within the patient's body. In other embodiments, the inner layer is attached to the outer layer and inserted together into a patient's body.

In some embodiments, multiple stents, each having multiple covers, e.g., shingled covers, are placed in vivo inside each other in a telescoping fashion to further minimize the risk of leaks through or around the covers. In some embodiments, there may also be an additional substance, including but not limited to hydrogel, which coats some or all of the frame and/or the covers, which can swell in vivo and further minimize the chance of leaks between shingles and/or between the stent or stents and the vessel wall.

In preferred embodiments, the stent is self-expanding. In other embodiments it can be balloon-mounted and balloon expandable. In some embodiments it is partly and/or fully re-sheathable. It may optionally be attached to a pusher wire. It may also be detachable via mechanical, hydrostatic, electrical, thermal, or other modalities.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
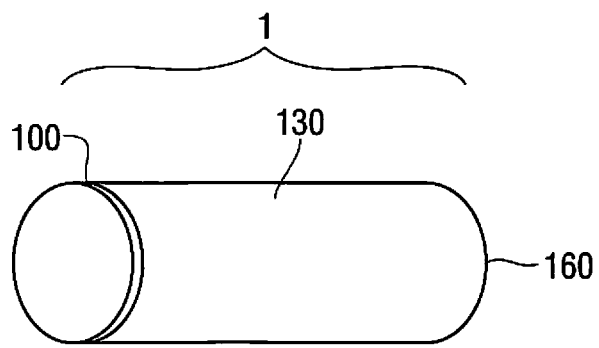
FIG. 1 is a perspective view of a cover of the caped (covered) stent in accordance with one embodiment of the present invention.

The present invention provides a covered (caped) stent configured for delivery through vessels, such as tortuous vessels, for deployment in vessels to effectively divert blood flow away from an aneurysm, fistula, or ruptured vessel while allowing blood to flow to healthy tissue distal to the targeted treatment area and still resulting in blood stasis and thrombus formation inside the aneurysm, fistula, or other covered lesion, or otherwise sealing closed an unwanted hole or outpouching. The covered stents of the present invention can be utilized in the neuro-vasculature as well as in other tortuous anatomy outside of the brain, in luminal structures and in other anatomies.

The covered (caped) stents of the present invention reduce or prevent kinking of the stent body (frame) as it bends due to the curves in the vasculature. This increased flexibility of the covered stents of the present invention is achieved by the attachment and configuration of the covers which provides a free-floating cover over the stent body. That is, the attachment of the cover to the stent body is minimized, thereby leaving a region that is unattached and free-floating. In this manner, when the covered stent is bent, the cover does not restrict the bendability of the stent body, but accommodates for such bending.

The covered stents of the present invention can move at sharper angles than covered stents of the prior art. The covered stents of the present invention present no sharp edges, and are prone to less kinking, thereby reducing risks of abrasion, puncture, rupture, narrowing, occlusion, or other damage to the target vessel, while allowing better conformance to the vessel wall in addition to a continuous seal. It also allows safe and effective delivery and deployment in many vessels that are more tortuous than what current stents permit. In some embodiments, the seal to the vessel wall may be further enhanced via a full or partial coating of hydrogel or another substance. The cape/cover design/configuration of the present invention eliminates, or at least ameliorates, rigidity associated with covered stents by allowing free movement of the cover (cape) in comparison to covers of the prior art which are attached along a length, attached at multiple points, or attached at opposing ends. This feature allows the user easier deployment of the covered stent of the present invention than existing covered stents of the prior art because existing stents have covers limiting bending, thus increasing stiffness. Furthermore, in stents of the prior art with fixed and fully attached coverings, the fixation of the covering (covering attachments) to the frame does not allow appropriate lengthening of the stent along the outside of a curve and corresponding shortening of the stent along the inner curve which makes stents of the prior art stiffer and more difficult to deliver and deploy in tortuous anatomy. In other words, the fixed and fully attached coverings of prior stents restrict the bending of the stent while in the covered stents of the present invention, the free ends, and thus free movements of the stent frame relative to the covers, enable more or full flexibility of the stent.

The present invention contemplates the use of one or more covers over the stent body. When a plurality of covers are provided, they can be arranged in an overlapping configuration as described in detail below. The overlapping configuration is also advantageous for controlled delivery of the stent as described below since the stent can maintain its flexibility when only one of the covered portions is deployed in the vessel. The covers can be of various configurations and can cover varied amounts of the stent body, also discussed in detail below. Some stents may have fenestrations in the covers and/or the frame as well.

Referring now to the drawings and particular embodiments of the present disclosure, wherein like reference numerals identify similar structural features of the devices disclosed herein throughout the several views, there are illustrated several embodiments of the covered stents of the present invention.

Figure 2:
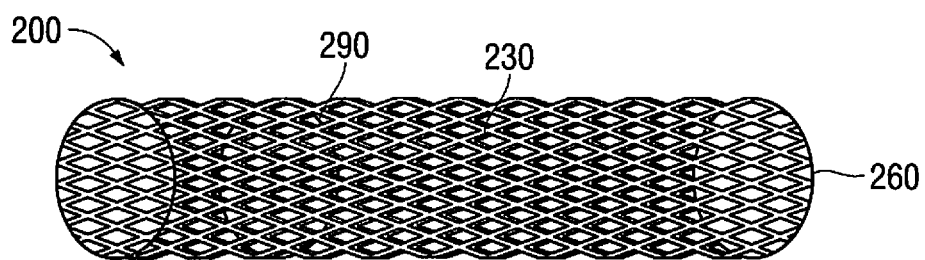
FIG. 2 is a perspective view of a stent (frame) of the caped (covered) stent in accordance with one embodiment of the present invention.
Figure 3:
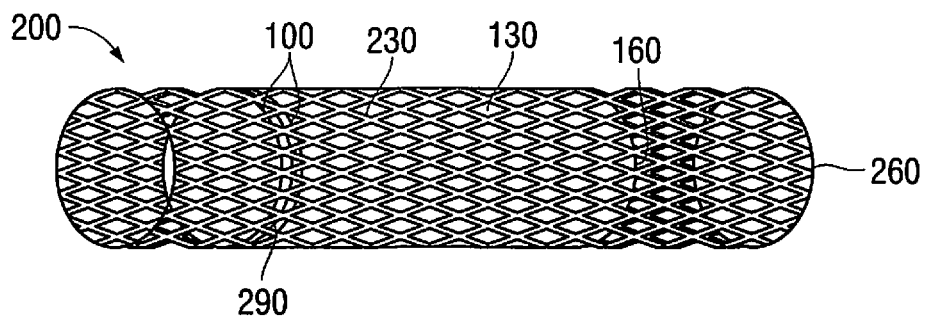
FIG. 3 is a perspective view showing the cover of FIG. 1 positioned within the stent body of FIG. 2.

Referring initially to FIGS. 1-3, a first embodiment of the caped (covered) stent of the present invention is illustrated. The cover or seal element 130 is shown in FIG. 1 and the stent body 230 is shown in FIG. 2. Preferably, such covers have limited or no porosity to blood and/or plasma. Note the cover 130, as well as the other covers disclosed herein, are also referred to herein as a "cape" or "sealing element" or "cape element." Also note the stent body 230, as well as the other stent bodies disclosed herein, are also referred to herein as the "stent" or "frame" or "stent frame" or 'skeleton" or "scaffold." The cover(s) are attached to the stent body, either internally such that they are attached to an inner wall of the stent body, or externally such that they are attached to an outer wall of the stent body, and/or in the interstices. Together, the device having the one or more covers attached to the stent body is referred to herein as the "caped stent" or "covered stent."

With continued reference to FIGS. 1-3, the cover (cape element) 130 has a connection or attachment element 100 at one end for attachment to element 290 on stent body 230. Various types of connections/attachment are contemplated such as welds, metallic string, fabric string and others. Opposite the end containing the connection element 100 is free end 160 which is not attached to the stent body 230. The cover 130 is preferably impermeable to provide a seal. It may also be permeable, partially permeable, or completely impermeable to various fluids and components.

Cover 130 can be of various lengths (from its attached end to its free end 160) according to the size of the target vessel, according to the desired area of the stent to be covered/sealed, and/or and according to the desired amount of flexibility in a region of the stent and/or according to the number of covers. The cover 130 in some embodiments is approximately 30% longer than the area of the target vessel intended to be covered in order to prevent rigidity at bends while allowing lengthening of the stent on the outer curve and still maintaining the desired coverage. More particularly, insofar as the cover 130 is only attached to stent 230 outside the seal-deployment area, the stent 230 will be more flexible than a stent having a cover attached or at multiple sites along its length. In alternate embodiments, the cover is more than 30% longer than the area of the target vessel to be covered. In other embodiments, the cover is less than 30% longer. Such various lengths of the cover, and various lengths of the extent of the stent body covered, are applicable to each of the covered stent embodiments disclosed herein.

FIG. 2 depicts the stent body 230 which is translucent, permeable and has a first end 200, a second end 260, and stent attachment element 290 closer to first end 200. The stent body 230 (as well as the other stent bodies (stent frame/skeleton) disclosed herein) can be formed from a plurality of metal struts as shown. The stent 230 can alternatively be formed from a plurality of wires or from a cut, e.g., laser cut, tubular member, a woven mesh, a braid, a polymeric material or combinations of these or other materials and methods—either varying along its length or two or more different frame types welded together at one or more points. The stent body may have a single layer or two or more layers welded together at one or more points. Examples are described below.

The cover 130 can be shown attached inside (internal) the stent body 230 (FIG. 3), i.e., attached to an inner wall of the stent body 230, and positioned so it is spaced proximally from the first end 200 and distally of the second end 260 of the stent body 230. This leaves uncovered (exposed) stent regions at the proximal and distal regions. The length of the uncovered regions can vary. The cover can alternatively be positioned outside (external) the stent body, i.e., attached to an outer wall of the stent body, as in alternate embodiments discussed herein. There may be no uncovered segments in some embodiments as well.

Figure 3A:
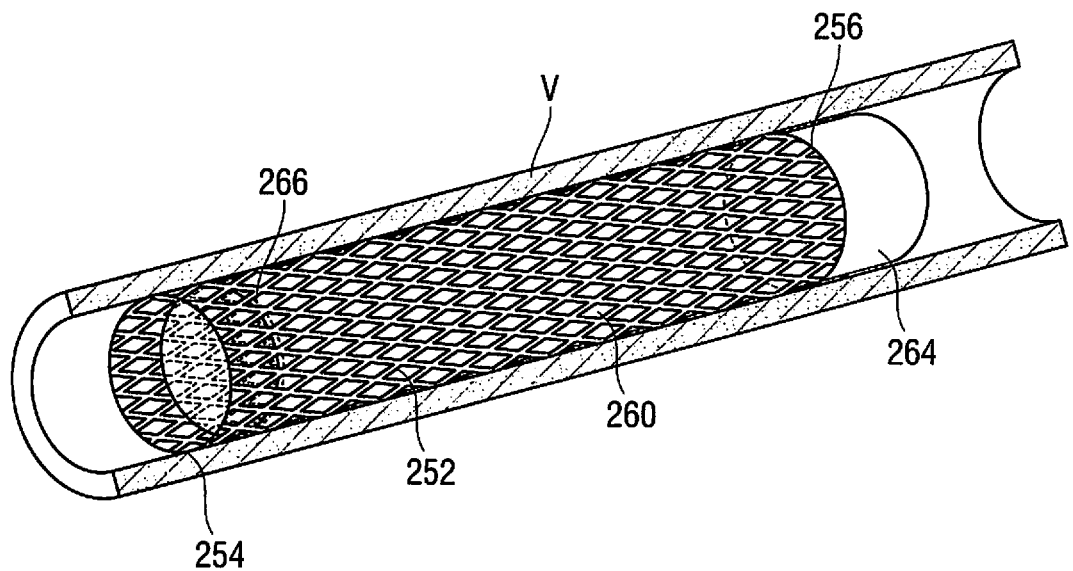
FIG. 3A is a perspective view of an alternate embodiment of the caped stent of the present invention wherein the cover is inside the stent (frame) and extends beyond a length of the stent, the caped stent shown inside a vessel.

The stent body 230 can be in the form of metal struts (or wires) which are collapsed during delivery through a delivery sheath or crimped onto a balloon to present a reduced profile and expand once delivered from the sheath to a larger diameter. The stent can be self-expanding or expandable by a balloon or other expanding mechanism/structure positioned within the stent. The expanded state is shown in FIGS. 2 and 3, with FIG. 3A showing an example of a covered stent expanded within vessel V.

Figure 4:
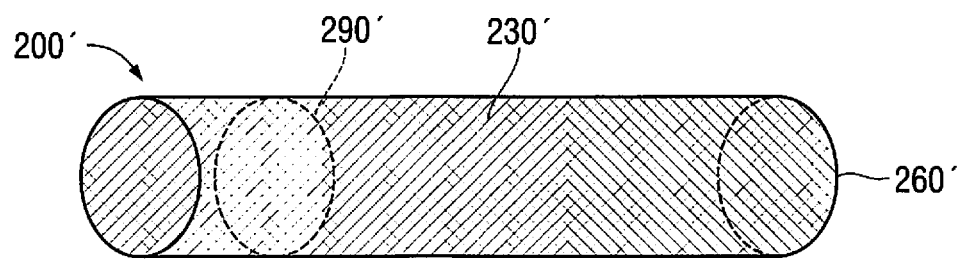
FIG. 4 is a perspective view similar to FIG. 2 except showing a mesh stent instead of stent formed of wire struts.
Figure 5:
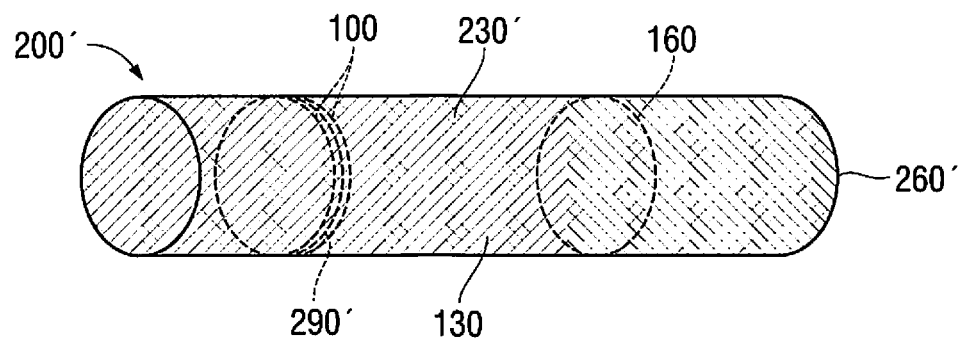
FIG. 5 is a perspective view showing the mesh stent of FIG. 4 having an internal cover attached at a distal end of the cover.

Alternatively, the stent body can be composed of a mesh with small permeable openings as in the embodiment of FIGS. 4 and 5. In this embodiment, stent body 230', like stent body 230 of FIG. 2, has a first end 200', a second end 260' and an attachment element 290'. In all other respects, the covered stent of FIGS. 4 and 5 is the same as the covered stent of FIG. 3. Cover 130 is positioned within the stent body 230'. However, alternatively it could be positioned outside the stent body as in the embodiment of FIGS. 5A and 5B. Covered stent 650 of FIG. 5A has a mesh stent 670 with a cover 660 positioned thereover and attached at attachment region 662 at a distal portion of the cover 660. Proximal region/end 664 of cover 660 and the remainder of the cover is unattached for free floating movement. The length of the attachment can vary from less than one nanometer to 1 meter. The cover 660 has a length less than a length of the stent body 670 leaving distal region 672 and proximal region 674 of stent body 670 uncovered. Other lengths and proportions are also contemplated.

Figure 5A:
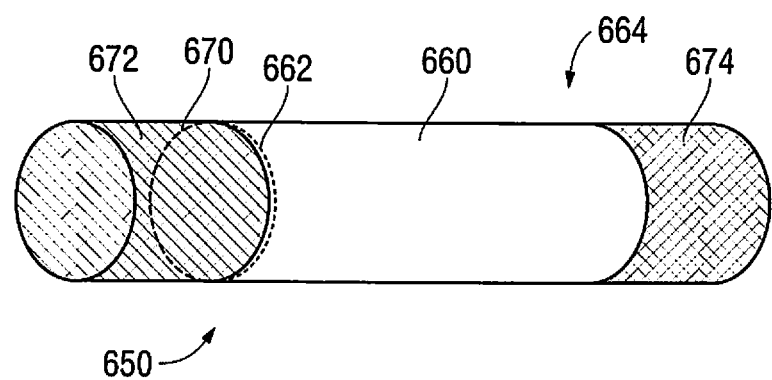
FIG. 5A is a perspective view similar to FIG. 5 except having a cover positioned over the mesh stent, the cover attached at a distal end of said cover.
Figure 5B:
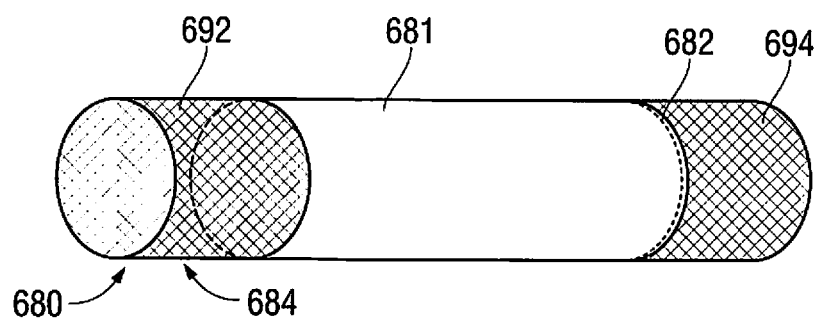
FIG. 5B is a view similar to FIG. 5A except the external cover is attached to the mesh stent at a proximal end of the cover.

Covered stent 680 of FIG. 5B is identical to covered stent 650 of FIG. 5A except that cover 681 has an attachment region 682 at a proximal portion/region of the cover 681 so that a distal region is free floating. Distal region 684 and proximal region 694 of stent body 692 are uncovered. As noted above, the length of the cover in this as well as in the other embodiments disclosed herein can vary from that shown and the cover can be placed closer toward a distal end or closer toward a proximal end rather than in a medial region as in FIGS. 5A and 5B. That is, the covers are shown over a medial portion of the stent body but alternatively can be positioned more distal or more proximal and can have a shorter or longer length than that shown. In any event, the covers are attached at one end region so that the opposing end region is free floating and can move relative to the stent body. There can also be a single cover, or multiple covers. In embodiments with multiple covers they can be fully overlapping, partly overlapping, not overlapping, and/or various combinations.

Note the mesh stent body of FIGS. 4-5B can be provided in any of the other embodiments disclosed herein.

Figure 3B:
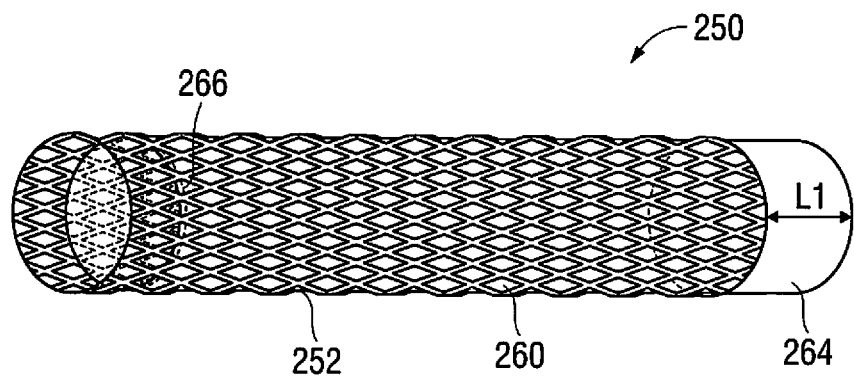
FIG. 3B is a perspective view of the caped stent of FIG. 3A.
Figure 3C:
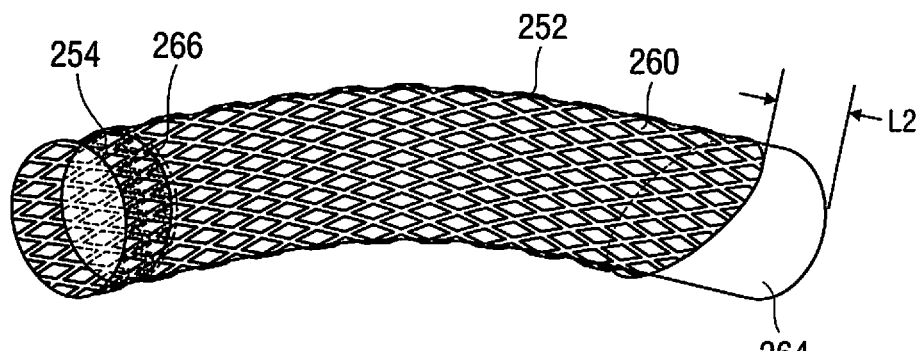
FIG. 3C is a view similar to FIG. 3B showing the free movement of the frame relative to the free portion of the cover when the caped stent is bent during insertion or use.

The advantage of the free end of the cover can be understood by comparing FIGS. 3B and 3C. In FIG. 3B, the covered stent 250 is in a straight/linear position. (FIG. 3A shows the covered stent 250 in a linear position within vessel V). The cover 260 is attached to an inner wall of stent body 252 at attachment region 266. When the covered stent 250 is bent, e.g., bent around a curve in a vessel, the free unattached end 264 can move relative to the stent body, e.g., slide (e.g., axially) within the stent, as shown in FIG. 3C. Thus, proximal region 264 of cover 260 slides within the stent body 252 so a shorter length L2 compared to length L1 is exposed as the stent lengthens along the outer curve. Along the inner curve, the stent frame body may shorten so the extent of coverage by the cover lengthens relative to the length of the stent frame/body along the inner curve. This enhances the flexibility of the stent since the bending is not restricted by the cover due to the relative movement of regions of the cover and the underlying (or overlying) stent body. That is, such movement maintains the flexibility of the stent since if the cover 260 was attached at both ends rather than having an unattached end for free movement, it would restrict bending of the stent body 252. This change is depicted in FIG. 3C—the cover relative "shortening" along the "outer" curve relative to the splaying and possibly lengthening stent frame, but relative "lengthening" of the cover relative to the stent frame along the "inner" (inferior) curve where the stent frame may shorten.

Note the free end can also be slightly longer to enable play upon bending of the stent body or otherwise allow movement. Note in this embodiment, the cover 260 extends beyond the proximal edge 256 of the stent body 252 so there is a region 264 not within the stent frame. At a distal end, the cover 260 is spaced proximally from the distal edge 254. Alternatively, the cover can extend distal of the distal edge 254 in lieu of or in addition to it extending beyond the proximal edge 256. Also, alternatively, the cover 260 can terminate within the stent body 252 so that it terminates at a proximal end distal of the proximal edge 256 of the stent body 252. In either case, the free end of the cover can move relative to the stent body and independently thereof.

Note the caped stent is shown in FIG. 3C in the expanded condition, it being understood however that the bend could occur during delivery at which state the stent would be collapsed/compressed to a condition having a smaller diameter within the delivery member to provide a lower profile for insertion. Once at the target site, it is released from the delivery member and can return to its expanded, e.g., larger diameter, condition. The free floating movement of the unattached region of the stent can occur in the delivery and/or placement positions of the covered stent.

Figure 3D:
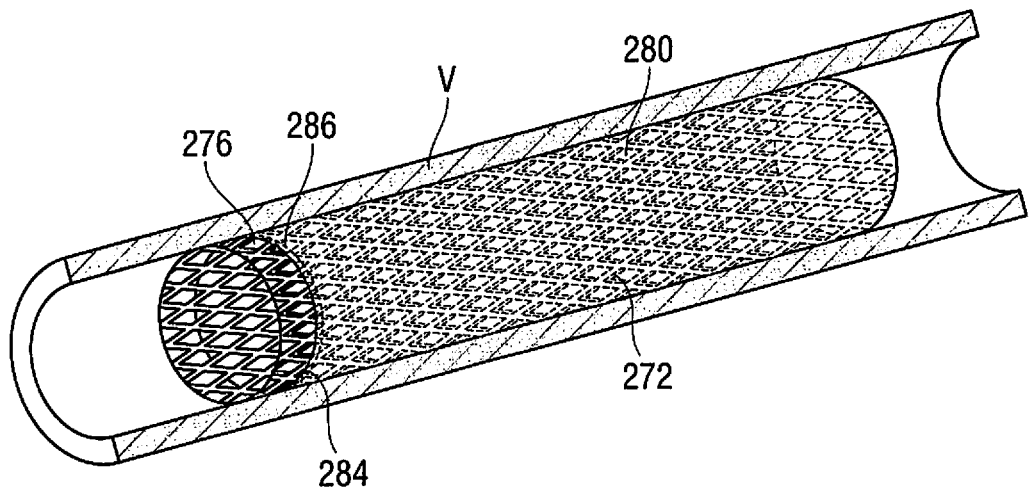
FIG. 3D is a view similar to FIG. 3A showing an alternate embodiment of the caped stent of the present invention wherein the cover is outside (external) the stent body, the caped stent shown inside a vessel.
Figure 3E:
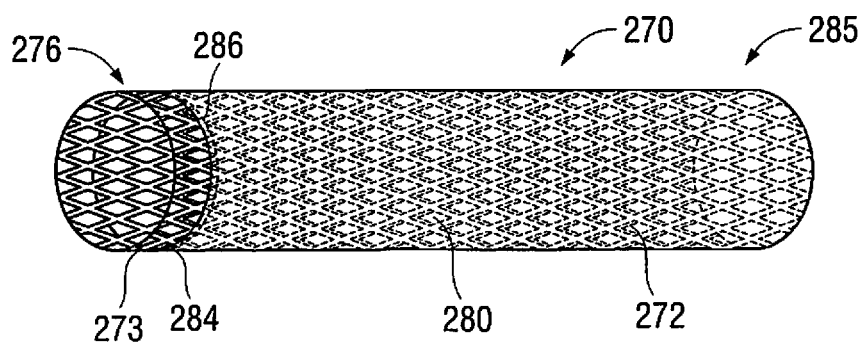
FIG. 3E is a perspective view of the caped stent of FIG. 3D shown outside the vessel.
Figure 3F:
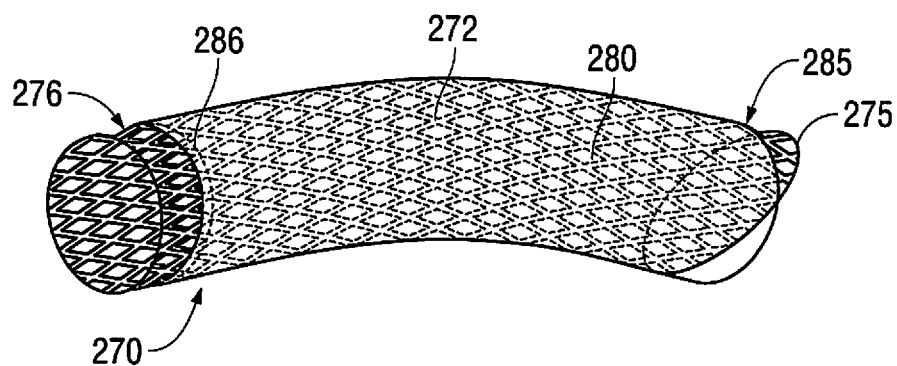
FIG. 3F is a view similar to FIG. 3E showing the free movement of the cover when the caped stent is bent during insertion or use.

As noted above, the cover can alternatively be placed outside the stent body to attach to the outer wall of the stent body. This is shown for example in the embodiment of FIGS. 3D-3F. Covered stent 270, shown within the vessel V in FIG. 3D, has a stent body 272 and a cover 280 attached at attachment region 286. Distal end 284 of cover 280 terminates proximally of distal edge 273 of stent body 272, leaving distal region 276 of stent body 272 uncovered. Alternatively, or in addition, a proximal region of stent body 272 could be uncovered. The length of the uncovered regions can vary so that the exposed regions are of greater length or of a smaller length. Also, the cover 260 is shown attached at its distal end but alternatively could be attached at a region spaced from the end or at a proximal end. Such alternate attachment locations are applicable to other covered stents disclosed herein. FIG. 3F illustrates the covered stent 270 when bent to illustrate movement of the stent body relative to the free end of the cover 280. When bent, free unattached end 285, on an end opposite the end of the attachment region 286, moves relative to the stent body 272 as can be seen by the exposed region 275 of the stent body (as compared to FIG. 3E), as the stent body flexes and may elongate and/or shorten along certain sections. As shown, lengthening of the stent along the outer curve decreases the length of coverage of the cover 280 relative to the stent body, along the outer curve; the shortening of the stent body along the inner curve may increase the proportion of the length of the frame covered along the inner curve, as shown. The relative positions of the stent body and cover at distal region 276 remains unchanged due to the cover attachment region 286 adjacent the distal region 276.

Figure 3G:
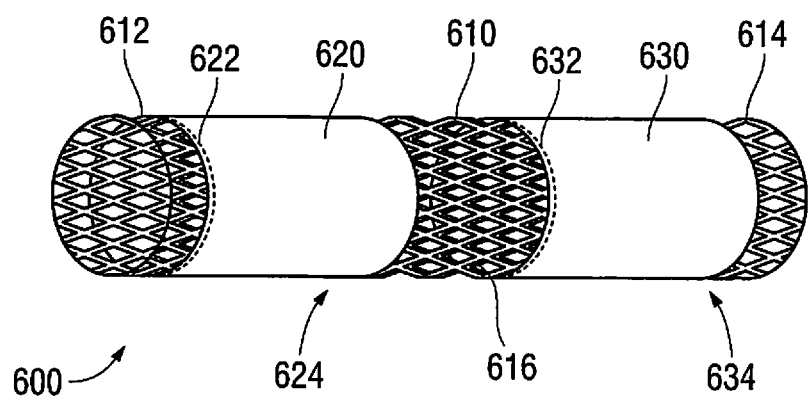
FIG. 3G is a perspective view of an alternate embodiment of the caped stent of the present invention having two external axially spaced covers.

In the alternate embodiment of FIG. 3G, two stent covers 620 and 630 of covered stent 600 are attached to stent body 610. The stent covers 620 and 630 are axially spaced to leave a medial region 616 of stent body region 610 uncovered. Cover 620 is attached at a distal attachment region 622 so that the opposing end 624 is unattached and free floating. Cover 630 is attached at distal attachment region 632 so that opposing end 634 is unattached and free floating. The covers 620 and 630 can be of the same or varying lengths, can be of different lengths than that shown and can be spaced differently than that shown to leave regions of alternate lengths of the stent body 610 covered and uncovered. It is also contemplated that more than two covers can be placed inside or outside the stent body at radially spaced intervals.

Figure 6:
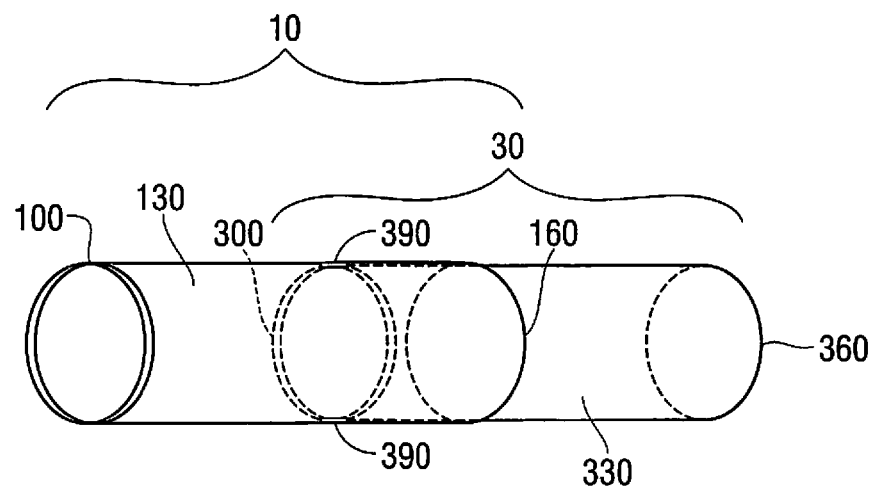
FIG. 6 is a perspective view of an alternate embodiment of the covers of a caped stent of the present invention, the covers shown in overlapping arrangement.
Figure 7:
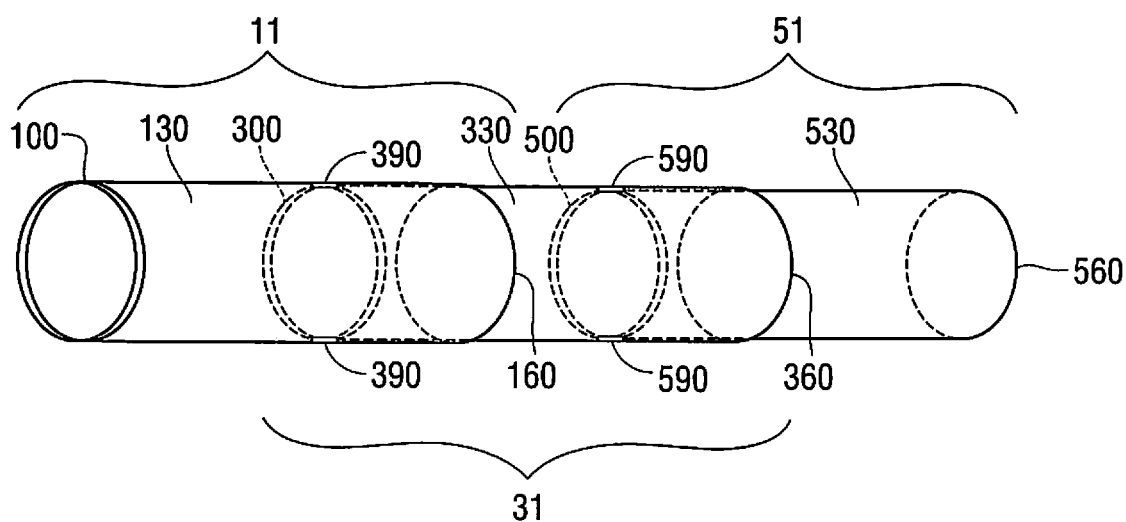
FIG. 7 is a perspective view of an alternate embodiment of the covers of a caped stent of the present invention, the three covers shown in overlapping arrangement.
Figure 8:
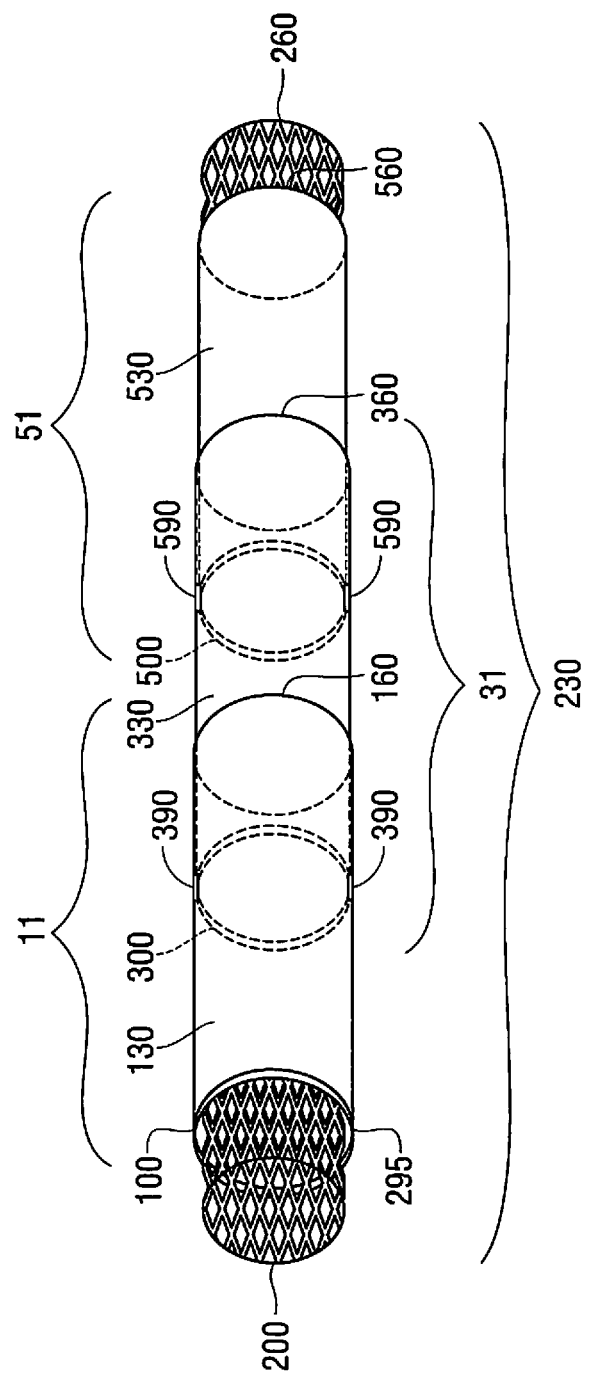
FIG. 8 is a perspective view of the caped stent of the present invention showing the three covers of FIG. 7 over the stent body with ends of the stent body uncovered.

FIGS. 6-16 illustrate alternate embodiments of the covered stents of the present invention wherein multiple stent covers are provided, arranged in partially overlapping fashion. In the embodiments of FIGS. 6-8, the stent covers are arranged axially along a longitudinal axis of the stent body so that a first stent cover is distal of a second stent cover, the second stent cover is distal of the third stent cover, etc. In the embodiments of FIGS. 9-13, the covers are arranged radially about the stent body, i.e., oriented circumferentially upon a longitudinal segment of the stent body, wherein each of the covers extend partially about the circumference of the stent body to cover less than a full circumference, and is overlapped by an adjacent cover extending around the same longitudinal segment. Thus, the cover is overlapped along a given length (longitudinal region) of the stent body. Stated another way, the covers can overlap longitudinally, in the manner of a fanfold or unrolled map. In each of the embodiments of FIGS. 6-16, the extent of coverage of the stent body changes as the stent bends, as well as depends on the amount of stent expansion allowed by a particular luminal diameter of the vessel (or other body region) the stent is disposed within. The free movement of the covers increases the flexibility of the stent. As in FIGS. 3C and 3F discussed above, when the stent bends, the coverage may relatively shorten along the outer curve as the outer curve length of the stent body increases and the coverage may relatively lengthen (increases) along the inner curve as the inner curve length of the stent body decreases.

Figure 6A:
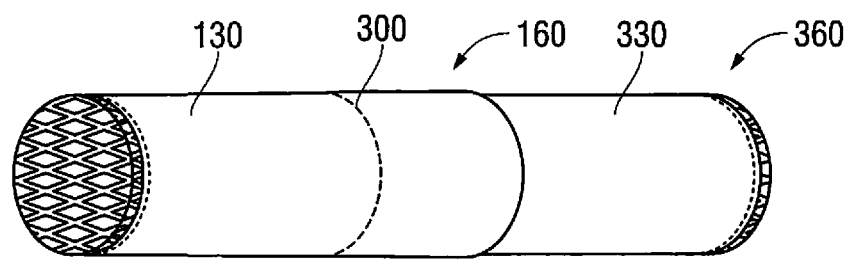
FIG. 6A is a perspective view of a caped stent of the present invention showing the covers of FIG. 6 positioned over the stent body.

Turning first to FIGS. 6 and 6A, the covered stent has a cover/cape 130 and a cover/cape 330. Cover 130 is attached at a distal end at attachment region 100 leaving a free end 160. A proximal portion of the cover 130, which includes the free end 160, overlaps a distal portion of cover 330. Cover 330 is attached at a distal region at attachment region 390 leaving free end 360 at a proximal portion. In the illustrated embodiment, cover 130 overlaps/overlies attachment region 390 of cover 330. Stated another way, the attachment region 390 and the distalmost edge at distal region 300 is overlapped by outer cover 130. The lengths of the stent covers 130, 330 are designated by references numerals 10, 30, respectively, to show the overlap. Note the length of the overlap region, in this and the other embodiments disclosed herein, can vary from that illustrated. It may also vary in the same stent depending on the configuration and/or bending of the stent. As can be appreciated, the free end 360 of cover 330 which is not attached to the stent body is unrestricted as it is exposed, i.e., not overlapped, by cover 130.

Figure 7A:
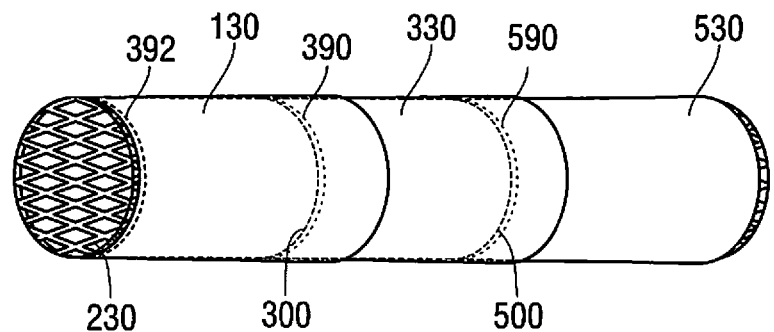
FIG. 7A is a perspective view showing the covers of FIG. 7 over the stent body.
Figure 7B:
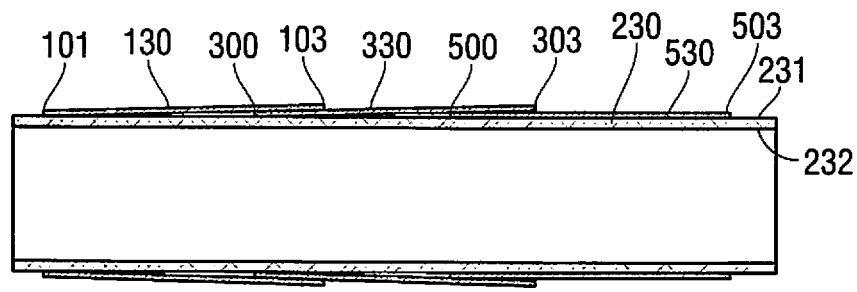
FIG. 7B is a longitudinal cross-sectional view of the caped stent of FIG. 7A.

FIGS. 7, 7A and 7B show how three caped elements can be coupled. In particular, the covered stent has a distal cover/cape 130, an intermediate cover/cape 330 and a proximal cover/cape 530. Cover 130 is attached at a distal end at attachment region 100 (adjacent the distal edge) leaving a free exposed/uncovered end 160. A proximal portion of the cover 130, which includes the free end 160, overlaps a distal portion of cover 330. Cover 330 is attached at a distal region 300 at attachment region 390 (adjacent the distal edge) leaving free end 360 exposed (uncovered). A proximal portion of the cover 330, which includes the free end 360, overlaps a distal portion of cover 530. Cover 530 is attached at a distal region 500 at attachment region 590 (adjacent the distal edge) leaving free end 560 exposed (uncovered). In the illustrated embodiment, cover 130 overlaps/overlies attachment region 390 and cover 330 overlaps/overlies attachment region 590. The lengths of the stent covers 130, 330 and 530 are designated by references numerals 11, 31 and 51, respectively, to show the overlap. Note the lengths of the overlap region, in this and the other embodiments disclosed herein, can vary from that illustrated. As can be appreciated, the free ends 160, 360 and 560 are unrestricted as they are exposed, i.e., not overlapped by the adjacent cover. The attachment regions 100, 300 and 500 are attached to the stent body and can be attached along a small longitudinal segment as designated by attachment regions/segments 100, 390, 590 (and at the distal region of cover 130 (not shown). The overlapping covers, which are arranged in a shingle-like arrangement, can be appreciated in the longitudinal cross-sectional view of FIG. 7B which shows proximal region 103 of cover 130 overlapping distal region, including distal attachment region 300, of cover 330 and proximal region 303 of cover 330 overlapping distal region, including distal attachment region 500, of cover 530. Proximal regions/free ends 303 and 503 of respected covers 330, 530 are not covered by a cover. The covers 130, 330 and 530 are attached to outer wall 231 of stent body 230. In alternate embodiments, one or more of the covers can be attached to the inner wall 232 of stent body 230.

FIG. 8 illustrates stent 230 positioned within the covers of FIG. 7. The covers 130, 330 and 530 can be attached to stent 230 at a single circumferential point attachment such as attachment point 295 for cover 130. That is, they are preferably attached at only one end which can be along a single circumferential ring or alternatively can be attached along a short length (longitudinal segment) of a distal region such as regions 390 and 590. Such single circumferential or longitudinal attachment point, combined with said overlapping circumferential shingles allows the stent to bend without kinking. Note the attachment point could alternatively encompass a full circumference, a partial circumference, a partial length, and/or combinations thereof, provided there is a sufficient free end region. Element 100 of first cover 130 fixes cover 130 to the stent body at stent attachment element or region 295, located on stent 230 between first end 200 and second end 260. Elements 390 and 590 are likewise attached to stent attachment elements, either at a ring-like attachment region such as attachment region 295 for cover 130 or along a longitudinal segment. Note the covers in FIG. 8 together cover less than a full length of the stent body 230, leaving uncovered distal and proximal regions. Other lengths are also contemplated.

Figure 13:
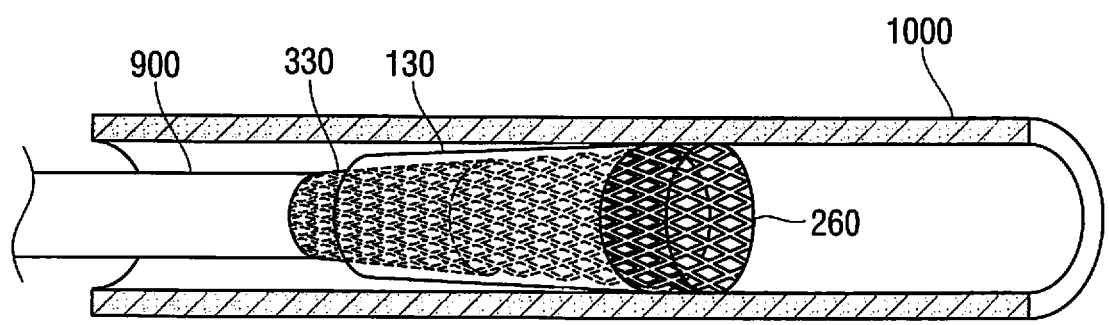
FIG. 13 is a side view of a self-expanding stent body of a covered stent of the present invention in the process of deployment from a delivery device.

The overlapping shingle arrangement can be used with balloon expandable (or mechanical expandable) and self-expanding stents. When a self-expanding covered stent is partially pushed out of the delivery device, e.g., catheter, and expands fully, it can pin the cover against the vessel wall. However, due to the shingled arrangement of the present invention, although a portion of the cover is exposed, and can be pinned against a vessel wall when that segment of the stent body fully expands, remaining portions or remaining covers can be maintained inside the catheter, which would then not be pinned yet against the vessel wall. In other words, the stent is not constrained as each cover (cape) can move independently so that pinning of one cover does not affect movement of the other covers. As the stent is unsheathed, the stent fully expands distally and the portion of the stent out of the catheter but immediately adjacent to it will still be somewhat constrained in circumference by the catheter's constraint of the immediately adjacent segment of the stent body. Each cover may be temporarily completely free of pinning/constraint from the catheter as well as the vessel wall as it comes out of the catheter, either by pushing the stent forward, withdrawing the catheter, or both pushing and withdrawing. Thus, the covers can be deployed in sequence as desired. Partial delivery of the covered stent to achieve this advantage is shown in FIG. 13. For example, when fully deployed from the delivery member (tube) 900, the first cape (cover) 130 can cover partially or fully a lesion prior to full deployment of the second cape (cover) 330. The first cape 130 as shown outside the delivery member 900 but not yet fully pinned between the stent frame and the vessel wall as a more proximal section (portion) of the stent remains constrained within the delivery member 900. The free end region of the cape 130 is still spaced from the vessel wall. The more distal section (portion) of the stent is shown deployed from the delivery member 900 so it expands into contact with the vessel wall. A distal portion of the second cover is exposed from the delivery member; a more proximal section remains inside the delivery member. As can be appreciated from the discussion herein, the free end does not restrict the stent bending. Also note that due to the series of shingled covers rather than a single cover, and due to the free end, when the stent is partially deployed if the distal cover becomes pinned to the vessel wall by the stent, the stent can still retain its flexibility as the other portions are deployed since the more proximal covers, with the unattached ends, will not restrict bending of the stent.

Figure 7C:
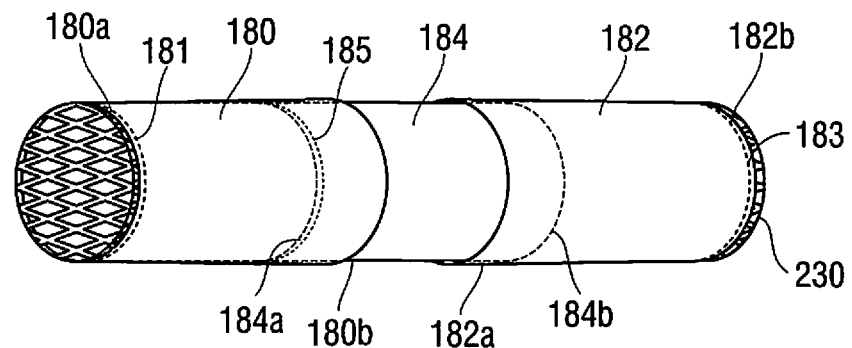
FIG. 7C is a perspective view of an alternate embodiment of the caped stent of the present invention having three covers in overlapping arrangement over the stent body, the proximal and distal covers overlapping the middle cover.
Figure 7D:
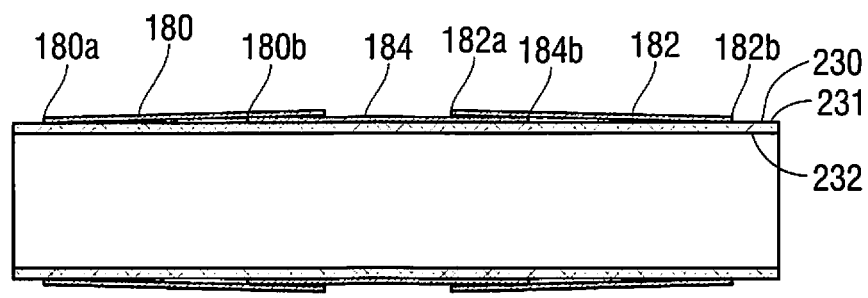
FIG. 7D is a longitudinal cross-sectional view of the caped stent of FIG. 7C.

The stent covers can overlap in various arrangements. One example of an alternate arrangement is shown in FIGS. 7C-7D. In this embodiment, distal and proximal stent covers 180 and 182 overlap intermediate stent cover 184, with a proximal region 180b of stent cover 180 overlapping a distal region, including distal end 184a, of stent cover 184 and a cover 182 overlapping a proximal region, including proximal end 184*b*, of cover 184. The stent cover 180 is attached adjacent distal end 180*a* and the opposite end 180*b* is unattached forming a free end at a proximal region. Stent cover 182 is attached adjacent distal end 182*a* leaving proximal end 182*b* unattached forming a free end. A portion of stent cover 184 is exposed. The stent cover 184 can be attached to the stent covers 180, 182, and/or attached to the stent body 230. Note alternatively, the cover 180 could be attached adjacent the proximal end 180*b* and/or the cover 182 could be attached adjacent the distal end 182*a* leaving the opposing ends free floating. The ends of stent cover 184 can be affixed to stent body 230 or alternatively one end can be attached and the other free floating. Covers are shown attached to outer wall 231 of stent body 230 but alternatively one or more of the covers could be inside the stent body 230 attached to the inner wall 232.

Figure 7E:
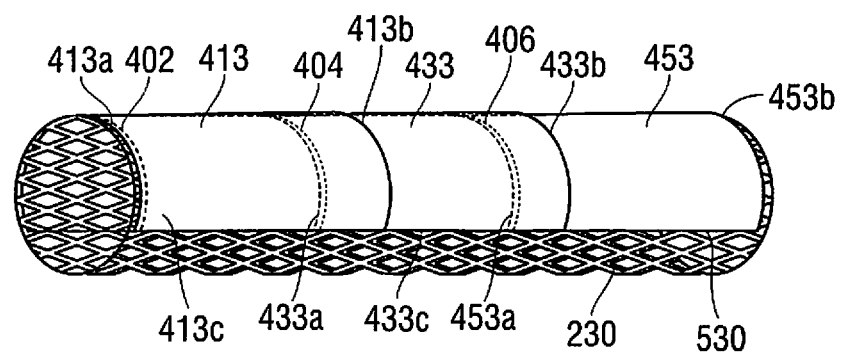
FIG. 7E is a perspective view of an alternate embodiment of the caped stent of the present invention having three covers in overlapping arrangement partially covering the stent body, i.e., extending less than 360 degrees about the stent body.

The covers as shown in FIGS. 6 and 8 extend around the full circumference, i.e., 360 degrees, of the stent body 230. In alternate embodiments, the stent covers extend externally around less than 360 degrees. This could include for example 270 degrees, 180 degrees and other amounts/ degrees about the stent body 230. FIG. 7E provides one example wherein the covers extend about 180 degrees around the stent body. The covers are configured as half cylinders and are arranged in a shingle like fashion as in the covers of FIG. 7A such that cover 413 overlies cover 433 and cover 433 overlies cover 453 (overlapping in a proximal to distal direction). More specifically, cover 413 has a distal end 413*a* attached to stent body 230 at attachment region 402 and a proximal unattached free end 413*b*, cover 433 has a distal end 433*a* attached to stent body 230 at attachment region 404 and a proximal unattached free end 433*b*; cover 453 has a distal end 453*a* attached to stent body 230 at attachment region 406 and a proximal unattached free end 453*b*. The proximal region of cover 413 overlies the distal region, including the distal end 433*a*, of cover 433 and the proximal region of cover 433 overlies the distal region, including distal end 453*a* of cover 453. In this manner, the shingle-like arrangement leaves the free ends of each cover 413, 433 and 453 exposed for free floating movement. Note the covers alternatively in this and other embodiments disclosed herein can be overlapped in a distal to proximal direction with attachment regions at the proximal ends.

The covers 413, 433 and 453 together cover the majority of the stent body 230, and extend from its proximal end to its distal end, although in alternate embodiments they can extend over a shorter length of the stent body. One or more of the covers can also alternatively be positioned within the stent body 230, attached to the inner wall instead of the outer wall, together extending for various lengths within the stent body 230. The covers can alternatively be attached at their proximal ends instead of their distal ends, leaving free floating unattached distal ends. Further note in this embodiment, as well as in other embodiments disclosed herein, the covers of the caped stent are shown of substantially the same length, however, alternatively these covers as well as the covers of the other caped stents disclosed herein can be of different individual lengths.

Figure 7F:
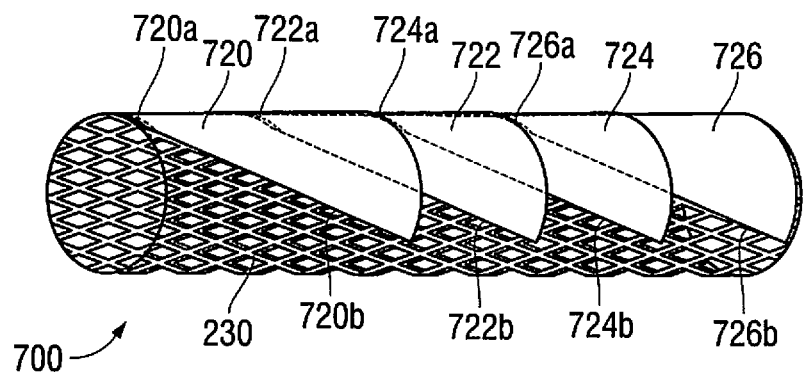
FIG. 7F is a perspective view of an alternate embodiment of the caped stent of the present invention having multiple covers in overlapping arrangement over the stent body, the covers being triangular shaped.
Figure 7G:
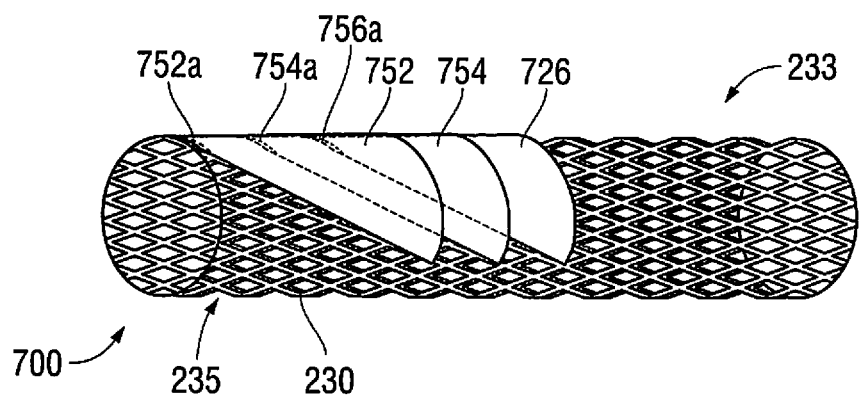
FIG. 7G is a perspective view of an alternate embodiment of the caped stent of the present invention having multiple covers in overlapping arrangement over the stent body, the covers being triangular shaped and covering less than a majority of the length of the stent body and extending less than 360 about the circumference of the stent body.

As noted above, the covers can be of various geometric shapes such as cylindrical or semi-cylindrical as illustrated in FIGS. 6-8. FIGS. 7F and 7G show the covers as triangular shaped to provide an illustrated example of a different shaped cover. FIG. 7F shows caped stent 700 having four substantially triangular covers 720, 722, 724 and 726 arranged in an overlapping shingle-like arrangement (like scales on a fish). Covers 720, 722, 724, 726 are attached at respective distal ends 720*a*, 722*a*, 724*a* and 726*a* leaving unattached free floating proximal ends. The proximal region of cover 720 overlies the distal region, including the distal end 722*a*, of cover 722, the proximal region of cover 722 overlies the distal region, including the distal end 724*a*, of cover 724 and the proximal region of cover 724 overlies the distal region, including the distal end 726*a*, of cover 726. Covers 720, 722, 724, 726 extend over less than 360 degrees of the stent body 230 terminating at respective edges 720*b*, 722*b*, 724*b*, 726*b*. It should be appreciated that a different number of covers could be provided. The covers can extend about the circumference of the stent body 230 different degrees (amounts) than that shown. That is, the covers in this and in the other embodiments could together cover a different amount of the stent body circumferentially and/or axially than the extent of coverage illustrated in the drawings.

Covered stent 750 of FIG. 7G illustrates an example wherein the triangular shaped covers together cover less than a majority of a length of the stent body 230, leaving longitudinal (axial segment region 233) exposed (uncovered) and covering less than the full 360 degrees of the stent body (leaving region 235 of stent body 230 exposed). Covers 752, 754, 756 are arranged in overlapping shingle-like arrangement. Covers 752, 754 and 756 are attached at respective distal ends 752*a*, 754*a*, 756*a* leaving unattached free floating proximal ends. Thus, the proximal region of cover 752 overlies the distal region, including distal end 754*a*, of cover 754 and the proximal region of cover 754 overlies the distal region, including distal end 756*a*, of cover 756.

The overlapping coverings to create an impermeable shingling effect as described herein enables each cover to be deployed completely, if desired, without fully deploying other covers. The advantage, for example, is that a fistula may be covered without fully deploying the entire covered stent. Another advantage of this feature is that it ameliorates the need for different-sized covered stents. Furthermore, the coverings can collectively cover longer lengths and/or diameters of a stent without significantly impeding the flexibility of the stent.

Figure 9:
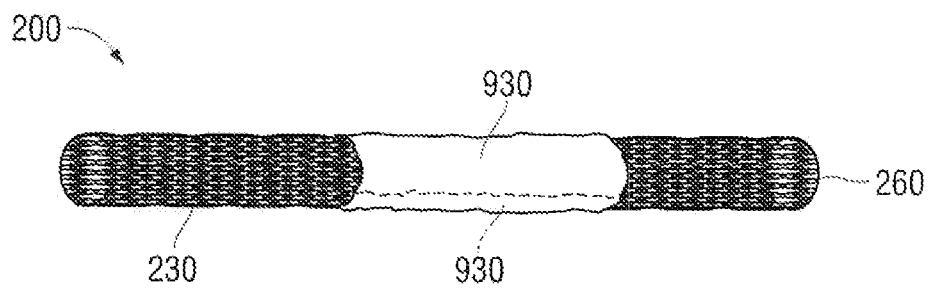
FIG. 9 is a perspective view of an alternate embodiment of the caped stent of the present invention having a series of covers arranged in circumferential overlapping arrangement, the covered stent shown in the collapsed delivery configuration (condition)
Figure 10:
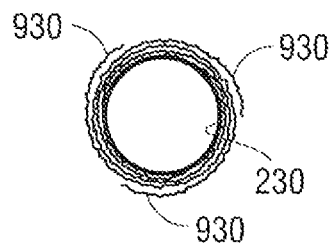
FIG. 10 is a cross-sectional view through a covered segment of the caped stent of FIG. 9 showing the covered stent in the collapsed delivery position.

FIGS. 6-7G show the stent covers extending along longitudinal (axial) segments of the stent body, overlapping in a shingle-like arrangement. In the embodiments of FIGS. 9-12, the covers overlap in a shingle-like arrangement circumferentially about the same longitudinal segment of the stent body. In FIGS. 9 and 10, the covers are shown in the rolled (undeployed) condition; in FIGS. 10A and 10B the covers are shown in the unrolled (deployed condition). Note in the "rolled condition" as defined herein, the covers are collapsed, i.e., are "wrinkled" or "bunched" so that they form an irregular non-even configuration. When deployed, the covers "unravel" to form a more regular and even cover about the stent body.

Figure 10A:
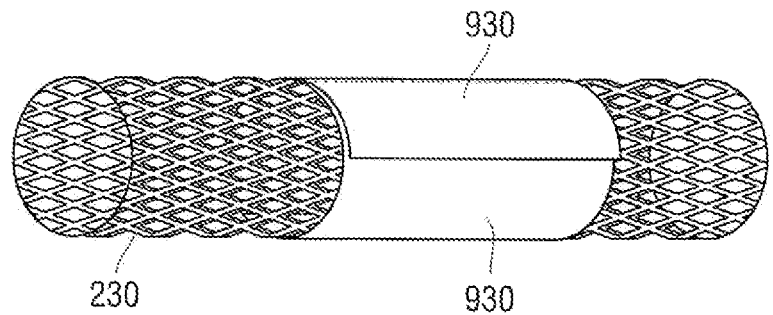
FIG. 10A is perspective view of the caped stent of FIG. 9 showing the covered stent in the expanded placement (deployed) configuration (condition)
Figure 10B:
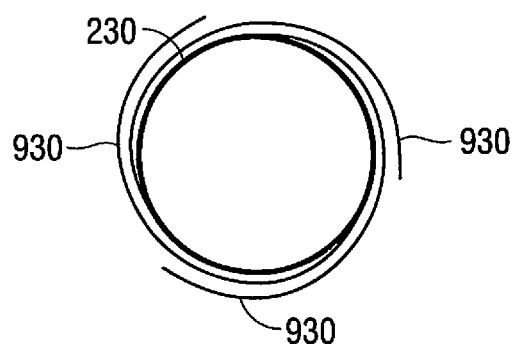
FIG. 10B is a cross-sectional view through a covered segment of the caped stent of FIG. 10A in the deployed configuration.

In FIGS. 9-10B, instead of having a single continuous cover there are multiple circumferentially "shingled" covers in the form of sheets of fabric, preferably substantially or entire impermeable, wherein the nonattached or free segment of sealing fabric from one sheet overlaps along an axial region with the attached segment of the adjacent sheet. This shingling allows the stent to more freely bend in zones where there is no attachment. The covers can be on the inner surface and/or outer surface of the stent body (frame) 230. Thus, the cover has multiple intermittent circumferential attachment points to the stent body 230, and has excess length of fabric at its free end compared to the "frame/ skeleton" in each segment between the attachments, to allow the skeleton to bend freely without being restricted by the fabric. The extra fabric will allow relative lengthening of the skeleton on the outer side of the bends of the stent within the vasculature. In some embodiments, the frame can be an open ended roll as well, which can allow some stents to conform to a greater variety of vessel diameters. That is, the stent frame may have a rolled configuration where the cylinder is not closed longitudinally.

More specifically, a plurality of covers 930 are attached to stent body 230 at linear connection points 935 on the outer surface of stent 230. The connection can be at the edges of each cover 930 at attachment 935 or alternatively can extend linearly from the edge along a longitudinal axis of the stent body 230, e.g., extending from the distal edge 933 to the proximal edge 936 of the cover 930. The stent covers 930 are positioned in a medial region of the stent body 230, between the ends 200 and 260. By extending less than the length of the stent body, a proximal region and a distal region of the stent body 230 are uncovered, although shorter or longer covered regions are also contemplated.

Figure 10C:
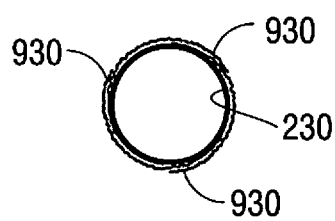
FIG. 10C is a cross-sectional view through a covered segment of an alternate embodiment of the caped stent of the present invention shown in the collapsed configuration.
Figure 10D:
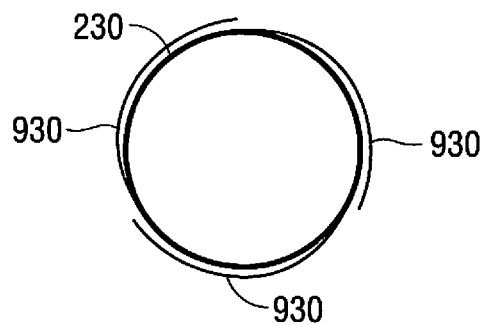
FIG. 10D is a cross-sectional view through of the caped stent of FIG. 10C shown in the deployed configuration.
Figure 11A:
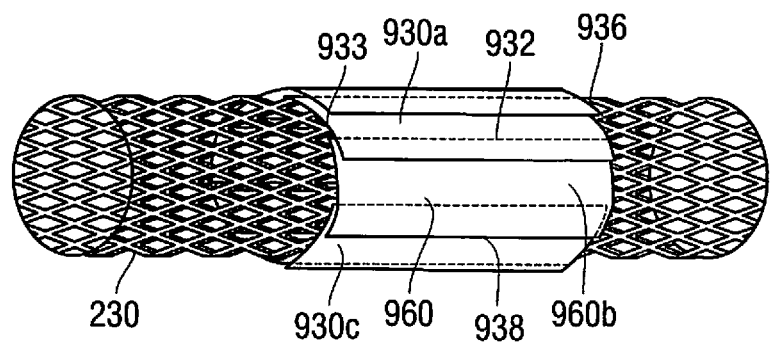
FIG. 11A is a perspective view of an alternate embodiment of the caped stent of the present invention having a series of covers in circumferential overlapping arrangement.

In the delivery (undeployed) position, each cover 930 is in a collapsed undeployed condition and the covers 930 extend around the circumferences of the stent body as shown in FIGS. 9 and 10 and are positioned in a medial region of the stent body 230. In some embodiments, the covers 930 are maintained in the undeployed condition within a delivery sheath (not shown) which constrains the covers 930 in the undeployed configuration. As shown in FIGS. 9 and 10, the covers in this collapsed position are irregular/wrinkled. The covers can extend over a minority or majority circumferential portion of the stent body, and in some embodiments can extend over 100% of the circumference (such as shown in FIG. 10). For example, they can extend over 360 degrees and over 125% of the circumference. Their degree of overlap will decrease when the stent is deployed and the covers likewise move to the deployed configuration (see FIG. 10A). By way of example, three covers can be provided each extending around ½ (180 degrees) of the stent body in the collapsed configuration and extending around ⅙ of the stent body when in the expanded deployed configuration. With the stent crimped, the covers would overlap more than when the stent is expanded and each cover could in some embodiments go all the way around the entire stent and even in some embodiments in the crimped position extend more than once around the stent body. FIG. 10C shows an alternate embodiment wherein the three stent covers in the collapsed configuration extend a shorter distance around the circumference compared to the embodiment of FIG. 10. FIG. 11A shows an embodiment having more than three covers around the stent body 230.

It should be appreciated, that a different number of covers, covers of different lengths, and covers extending around different amounts (degrees) of the stent body in the deployed and undeployed configurations of the stent are contemplated.

When deployed, the covers unroll (uncoil, unwrap) into the overlapping condition shown in FIGS. 10A and 11A. (The covers can unwrap as the stent expands). When deployed, cover 930a of the covers (collectively referred to by reference numeral 930) has an end region 960 with edge 932 forming a free end which overlaps an axial region of cover 930b, cover 930b has an end region or edge 938 which overlaps an axial region of the adjacent cover, etc. In this manner, each cover has a free axial region 960 from end 933 to end 936 which overlaps an axial region from end 933 to end 936 of an adjacent underlying cover. The line of attachment of the cover to the stent body 230, extending from first end 933 to second end 936, is represented by the dashed line in FIGS. 10A and 11A. Thus, each cover has an uncovered free end (region) 960 extending along a longitudinal (axial) length, i.e., extending along a longitudinal segment of the stent body 230. In this way, the plurality of unrolled seal elements (covers) 930 overlap such that each free end 960 makes a flap over the end at the adjacent linear connection points to form a fanfold-type overlap covered stent, thereby forming a coverage band of overlapping free ends 960 about the circumference of stent 230. Note the number of covers encircling the stent body 230 can vary depending on the dimensions of the cover and the desired amount of coverage. The length of the covers can also vary. As can be appreciated in FIGS. 10A and 11A, in the deployed position, the covers form a smoother more even outer surface as compared to the wrinkled irregular outer surface when collapsed.

Figure 11B:
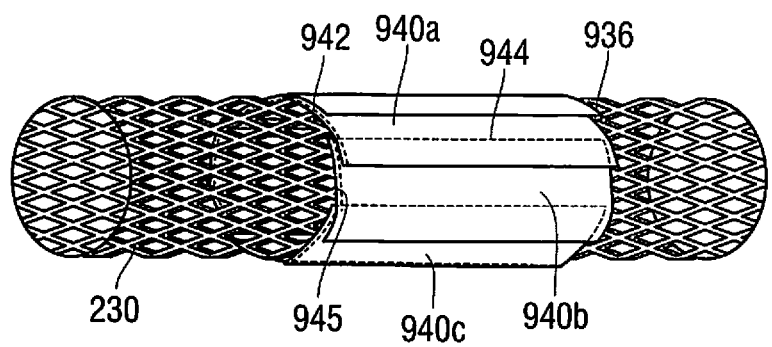
FIG. 11B is a perspective view of an alternate embodiment of the caped stent of the present invention having a series of covers in circumferential overlapping arrangement.
Figure 11C:
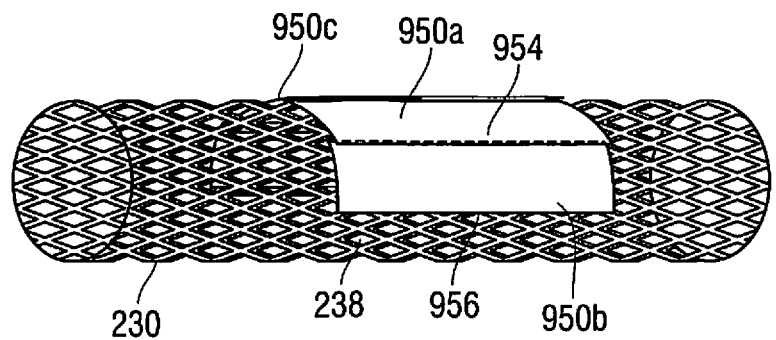
FIG. 11C is a perspective view of an alternate embodiment of the caped stent of the present invention having a series of covers in circumferential overlapping arrangement, the covers extending over less than the 360 degrees about the stent body.

FIG. 11B illustrates an alternate embodiment of the covered stent of the present invention. FIG. 11A shows an alternate embodiment having eight covers 930 as an example of a covered stent with multiple covers. As described above, three covers 930a, 930b, and 930c are each attached to a stent body 230 along a longitudinal segment 932 extending from edge 932 (or adjacent edge 932) to edge 936) or adjacent edge 936. The covered stent of FIG. 11B is identical to the covered stent of FIG. 11A except the covers 940 have an additional attachment. That is, the covers 940 differ from covers 930 by having an attachment region 945 at a distal end (or alternatively at a proximal end) which extend radially about the circumference of the stent body. In all other respects, covers 940a, 940b, 940c, etc. (collectively referred to as covers 940) are identical to covers 930 and overlap in the same manner as covers 930 as the axial overlapping regions extend from end 942 to end 936 (or adjacent these ends).

The covered stents of FIGS. 9-11B have covers which together extend around the entire circumference of the stent body 230 (the entire 360 degrees). In alternate embodiments, such covers can extend for less than 360 degrees such as for example 270 degrees, 180 degrees and other amounts/degrees about the stent body 230. FIG. 11C provides one example wherein the covers collectively extend about 180 degrees around the stent body, the coverage terminating along edge 956. The covers 950 are arranged in a shingle like fashion like the covers of FIG. 11A such that cover 950a overlaps cover 950b and cover 950a is overlapped by cover 950C. In this manner, a circumferential region 238 of stent cover 230 is exposed. Covers 950 are attached along an axial region or edge as shown in dashed lines 954.

It should be appreciated that in the circumferential overlap of the embodiments of FIGS. 9-1 IC, the covers can be placed at a medial portion of the stent or at a more distal region or at a more proximal region. They can also cover a majority or less than a majority of the axial length of the stent body as well as cover the entire or less than the entire circumference of the stent body. "Majority" as used herein denotes a range from more than 50% to 100%.

Figure 11D:
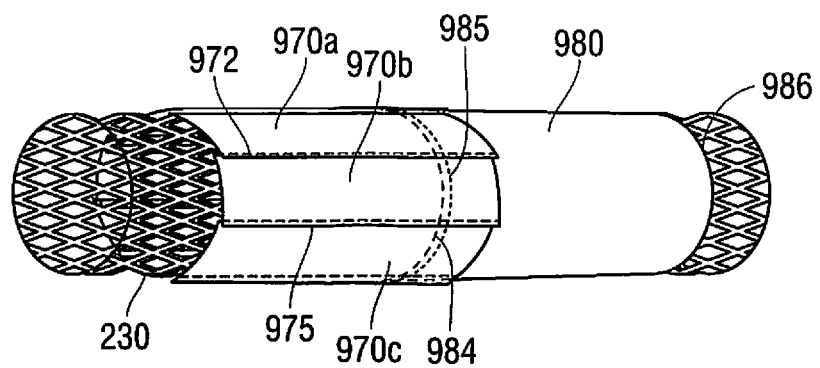
FIG. 11D is a perspective view of an alternate embodiment of the caped stent of the present invention having a series of circumferential overlapping covers overlapping a cover extending around the entire circumference of the stent body.
Figure 12:
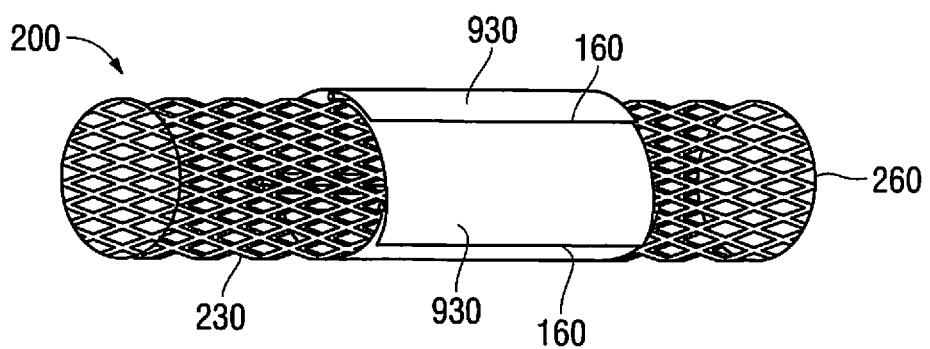
FIG. 12 is a view similar to FIG. 10A showing an alternate embodiment with additional covers, the covered stent shown in the deployed position (condition)

In the embodiment of FIG. 11D, the covered stent has circumferential overlapping covers 970a, 970b, 970c, etc. (collectively referred to as covers 970), overlapping in the same fashion as covers 930a, 930b and 930c of FIG. 11A. The covers 970 can have a coiled (wrapped) and unrolled uncoiled (unwrapped) configuration like covers 930. However, this embodiment differs from the embodiment of FIG. 11A in that an additional cover 980 is provided. Covers 970 overlap a distal region including distal edge 984 of cover 980. Cover 980 is attached about its circumference to stent body at distal region 985. Proximal end region 986 is unattached and forms a free end. Thus, in this embodiment, the covers 970 have free ends (e.g., ends 972, 975, etc.) extending along a longitudinal segment of the stent body 230 and cover 980 has a free end 986 extending circumferentially about the stent body. The free ends of the covers are exposed. Covers 970, 980 can cover the entire length of the stent body 230 or a portion, as in FIG. 11D, leaving distal and proximal regions of the stent body 230 exposed.

In some embodiments of the present invention a second stent can be provided which pins the cover between the exterior of the covered stent body and the interior of the second stent. This is shown for example in the embodiment of FIGS. 14-16. Covered stent 800 has cover 810 attached to the stent body 804 at a distal end at attachment region 811 (adjacent the distal edge 810a) leaving an unattached free end 810b. A proximal portion of the cover 810, which includes the unattached free end 810b, overlaps a distal portion of cover 812. Cover 812 is attached to stent body 804 at a distal region at attachment region 813 (adjacent the distal edge 812a) leaving a free end unattached end 812b. A proximal portion of the cover 812, which includes the free end, overlaps a distal portion of cover 814. Cover 814 is attached to the stent body 804 at a distal region at attachment region 815 (adjacent the distal edge 814a) leaving a free unattached end 814b. In the illustrated embodiment, cover 810 overlaps/overlies attachment region 813 and cover 812 overlaps/overlies attachment region 815. The stent body 804 forms an inner stent or inner frame. An outer stent 802 is placed over the covers 810, 812, 814 so that the covers are sandwiched between the inner stent 804 and outer stent 802. Note the lengths of the overlap region, in this and the other embodiments disclosed herein, can vary from that illustrated. Also, in some embodiments, the outer stent is positioned only over some of the covers or extends for a length less than the total axial length of the adjacent covers. The overlapping covers 810, 812, 814 are arranged in a shingle-like arrangement as can be appreciated in the cross-sectional view of FIG. 16 which shows the proximal region of cover 810 overlapping distal region, including distal attachment region 813, of cover 812 and the proximal region of cover 816 overlapping the distal region, including distal attachment region 815, of cover 814. Gaps 816 and 816a are shown between the outer surface of inner stent 804 and the inner surface of outer stent 802.

Figure 14:
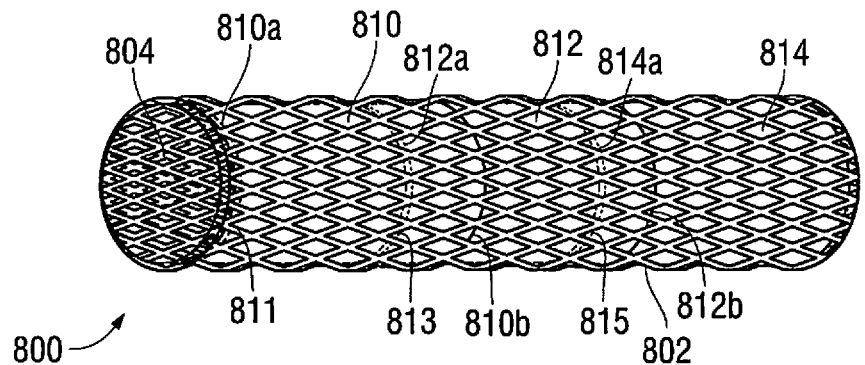
FIG. 14 is a perspective view of an alternate embodiment of the caped stent of the present invention having an outer stent overlying the covers covering the stent body.
Figure 15:
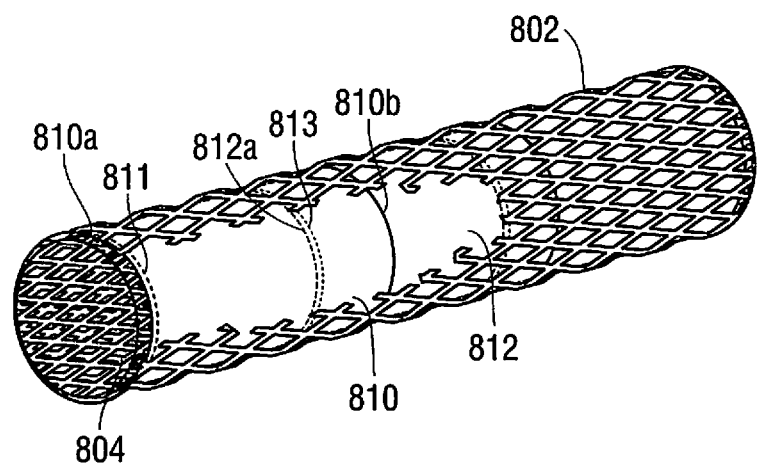
FIG. 15 is a perspective view of the caped stent of FIG. 14 with portions of the outer stent removed for clarity.
Figure 16:
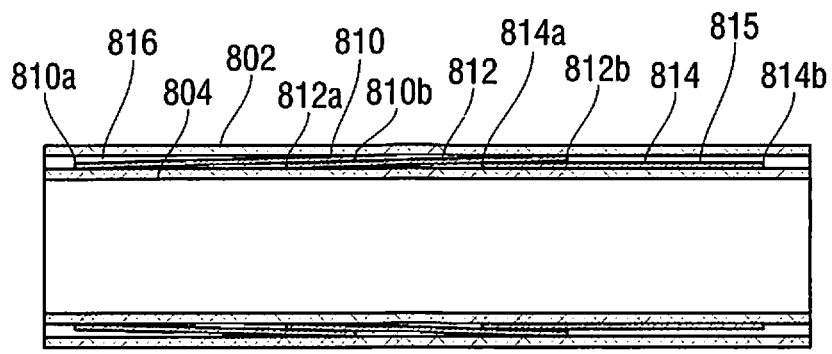
FIG. 16 is a longitudinal cross-sectional view of the caped stent of FIG. 14.

As can be appreciated, in the embodiments of FIGS. 14-16 the cover, e.g., the "fabric" is pinned between the two layers of stents. The second outer stent can either be a second built-in layer with the cover, e.g., fabric layer, sandwiched in between (but the fabric mostly unattached), or placed separately as a separate, non-attached layer. This second stent (skeleton) can often minimize the risk of endoleaks at the non-attached regions. Endoleaks can be minimized where the fabric layer is not fully attached—if a second stent does not pin the fabric to the first stent then some of the fabric layers may have some freedom of movement—especially in regions where they are covering an aneurysm or a fistulous hole and not pinned fully to a vessel wall. When they have some freedom of motion after implanted, blood flow can potentially sometimes flap them open, especially in the "shingled" version. In this two-layer configuration, with an inner stent that has outer cover(s), the outer stent can in some embodiments have no covers at all, but rather have a frame alone that will act similarly to a vessel wall to pin the cover(s) between the inner stent and the frame of the outer stent. In this case, a stent is over a vessel segment entailing a lesion, such as an aneurysm or a fistulous hole in the vessel, and is over the stent body of the inner stent. Alternatively, in this two layer configuration, with an outer stent that has inner cover(s), the inner stent can in some embodiments have no covers at all, but rather have a frame alone that will act similarly to a vessel wall to pin a cover between the inner stent and the stent body (frame) of the outer stent. Alternatively, one or both of the outer and the inner stents can have outer covers. In some embodiments, one or more covers are attached to an outer wall of the inner layer and/or are attached to an inner wall of the inner layer and/or are attached to an outer wall of the outer layer and/or are attached to an inner wall of the outer layer.

Figure 19A:
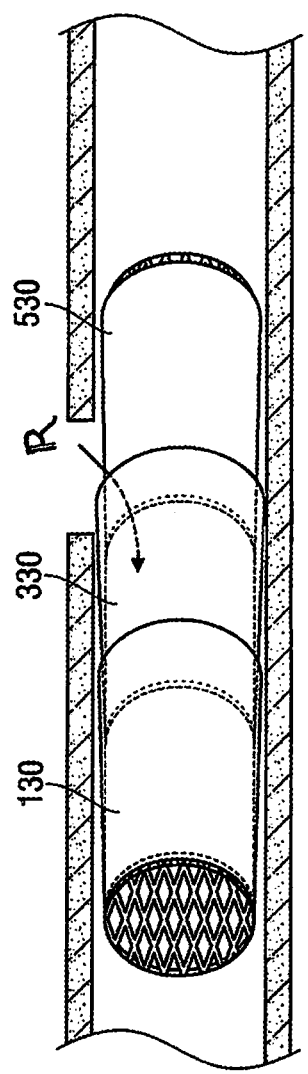
FIG. 19A is a perspective view showing a caped stent in accordance with an embodiment of the present invention positioned adjacent a vessel opening, the arrow depicting leakage under the middle cover.
Figure 19B:
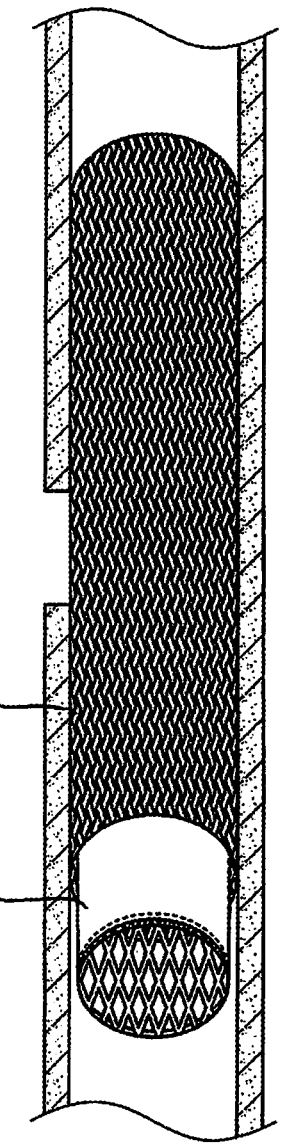
FIG. 19B is a view similar to FIG. 19A showing the caped stent positioned within an outer stent.

If a portion of the stent cover is not well apposed to a vessel wall, as can occur when it is overlapping a large fistula, a second similar covered stent can be placed inside the first covered stent, and the frame of the first covered stent will help secure the cover(s) of the second covered stent. Similarly, a different covered or uncovered stent can be used as the initial outer stent, provided such outer stent has small enough interstices that the cover(s) of the second inner stent cannot herniate through those interstices. Thus, is some embodiments, an additional stent with outer covers or no covers may be subsequently positioned inside another stent to help secure the covers and avoid vascular obstruction. An example is illustrated in FIGS. 19A and 19B. In FIG. 19A, the covered stent is shown positioned next to an opening in a vessel. This can be a fistula, an aneurysm, or other structure. In certain applications, the free end of one of the covers, e.g., the middle cover 330, can protrude a bit into the opening, thus enabling leakage of blood under the cover 330 (see arrow R). Such endoleak is prevented as shown in FIG. 19B by use of an outer stent 331. The outer stent 331 is positioned in the vessel, across the opening, and then the covered stent of the present invention is inserted within the outer stent. The covered stent can be that as described herein, and could have the cover on the inner wall and/or the outer wall. In the embodiment of FIG. 19B, the multi-layered stent could have an outer woven or braided stent and inner stent with larger openings formed by laser cut, a series of struts, etc. In some embodiments the porosity of the inner stent exceeds the porosity of the outer stent and the porosity could be between about 70% and about 99.9%, and more preferably greater than about 80% porosity, although a greater or smaller porosity is also contemplated. The porosity of the outer stent could be between 0% and about 80%, and more preferably be 75% or less, although a greater or smaller porosity is also contemplated.

The covered stents of the present invention could optionally include an additional structure to minimize endoleaks such as adhered hydrogel. The hydrogel can be in the form of a coating adhered to the stent, e.g., the stent body/frame (outer and/or inner stent body in embodiments with two stent layers) and/or the cover and/or to one or more of the covers if multiple covers are provided. An example of the hydrogel preventing endoleaks is if the cover has a fold when placed, and blood might be able to get through, the hydrogel could swell and fill the gap.

Figure 17:
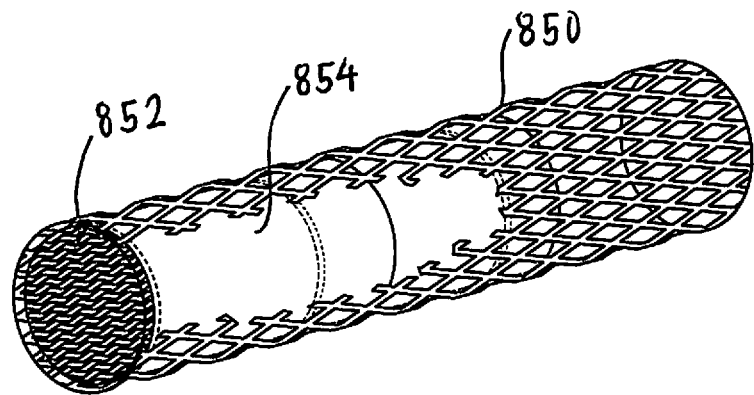
FIG. 17 is a perspective view of an alternate embodiment of the caped stent of the present invention having two stent layers, with a portion broken away to show the cover.
Figure 18:
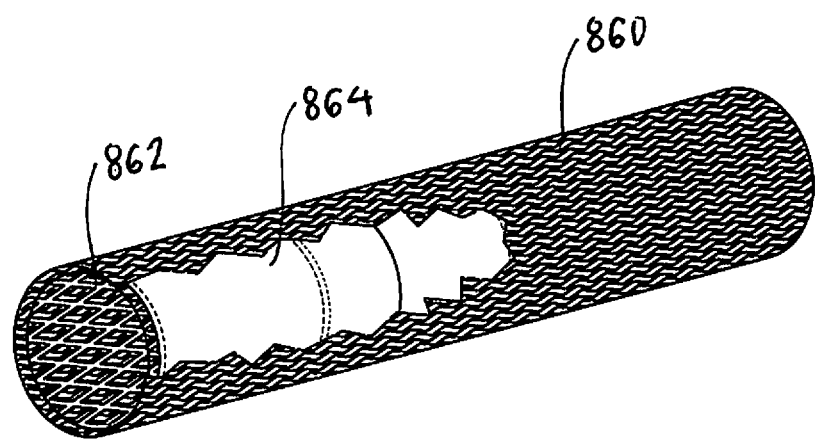
FIG. 18 is a perspective view of another alternate embodiment of the caped stent of the present invention having two stent layers, with a portion broken away to show the cover.

FIGS. 17 and 18 illustrate alternate embodiments of the multi-layered covered stent. In FIG. 17, the outer stent 850 is composed of a metallic material. It can be formed from a laser cut tube or by other methods and can be expandable via self-expansion or balloon or mechanical expansion. The outer stent can also be formed of other materials, including polymeric material. The inner stent 852 is formed of a woven material, e.g., a braid, and has less porosity than the outer stent. The porosity of the outer stent could in some embodiments by way of example be between about 70% to about 99.9% and more particularly could be 80% or more.

The inner stent could have a porosity less than 75% in some embodiments. The inner stent can also be formed of other materials. The one or more covers 854 are interposed between the two stents 850 and 852. In the alternate embodiment of FIG. 18, the outer stent 860 is formed from the woven material, e.g., a braid, and the inner stent is a metallic material formed from a laser cut tube or other methods. The inner stent can be formed of self expandable materials or formed of balloon expandable or mechanically expandable materials, including metallic or polymeric materials. The one or more covers 864 are interposed between the two stents 860, 862. In either of these embodiments, one or more of the covers can be attached to the outer wall of the outer stent, the inner wall of the outer stent, the outer wall of the inner stent and/or the inner wall of the inner stent, or combinations thereof.

Figure 20A:
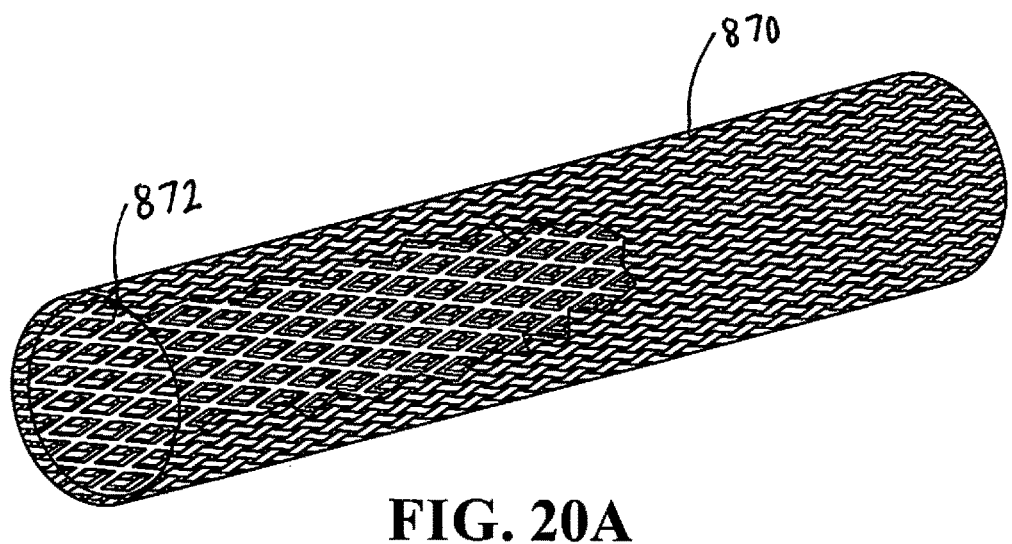
FIG. 20A is a perspective view of an alternate embodiment of the of the present invention having two stent layers, with a portion broken away to show the inner stent layer.
Figure 20B:
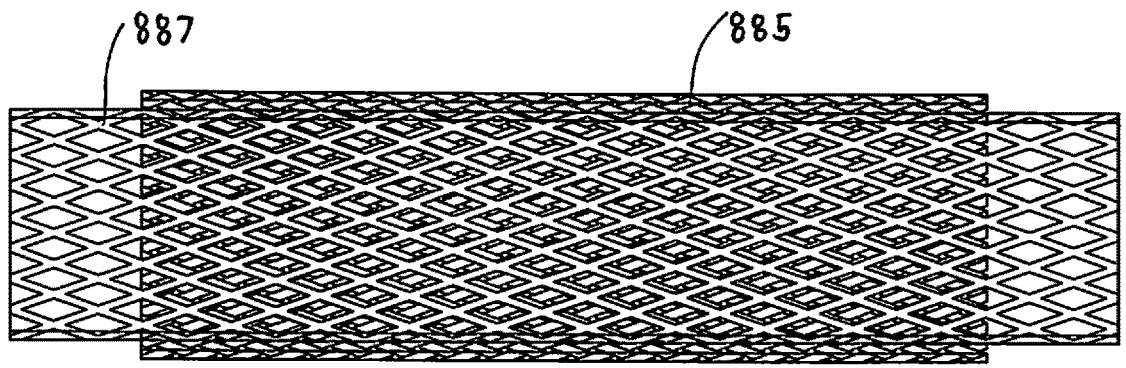
FIGS. 20B and 20C are cross-sectional and perspective views of an alternate embodiment of the present invention having two stent layers.
Figure 20C:
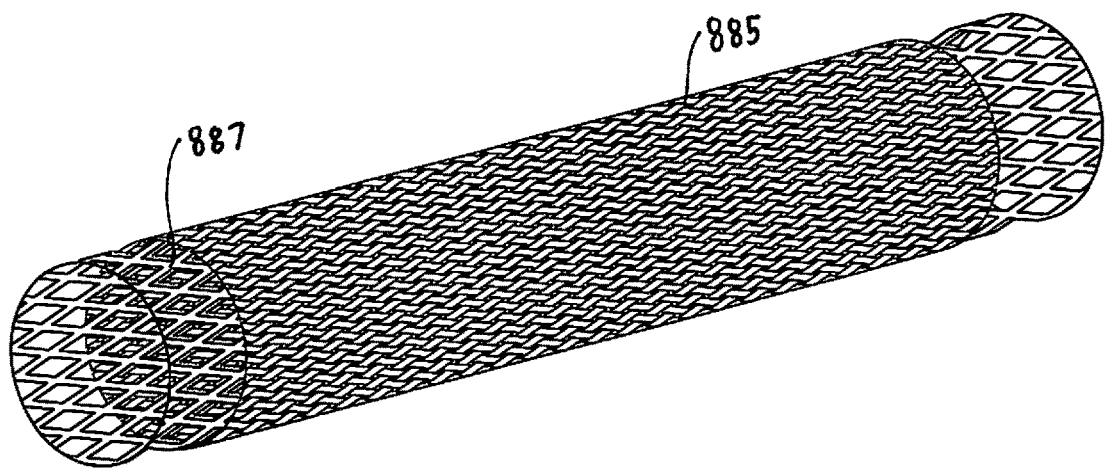
Figure 20D:
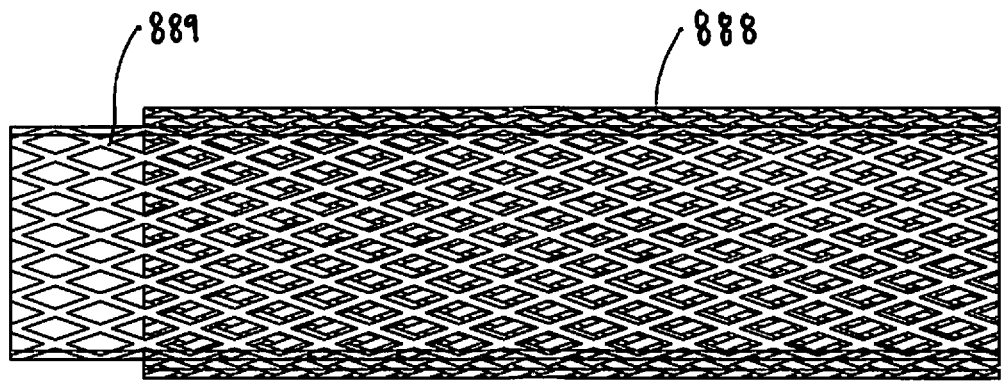
FIGS. 20D and 20E are cross-sectional and perspective views of another alternate embodiment of the present invention having two stent layers.
Figure 20E:
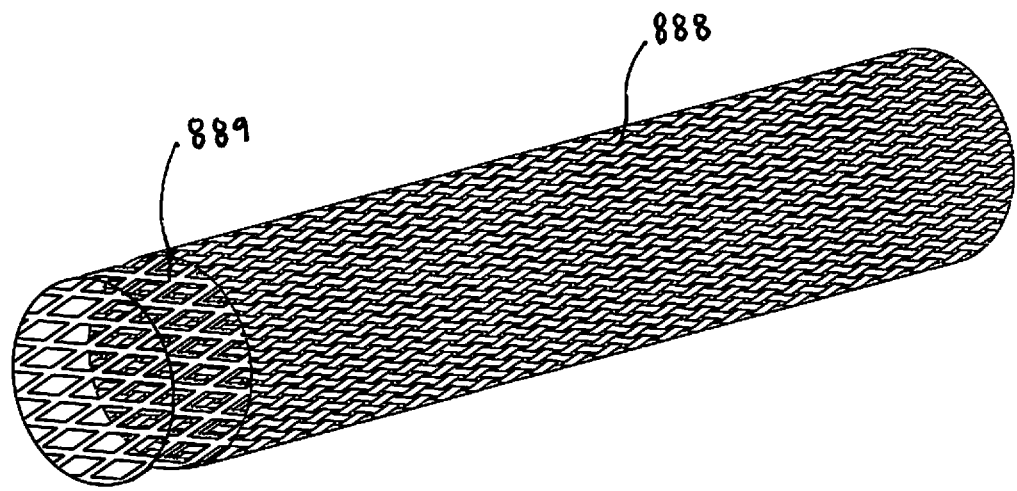

FIGS. 20A-20C illustrate alternate embodiments of the multi-layered stent without the covers. In these embodiments, the outer stent is formed of a woven material and the inner stent is more open, i.e., has a greater porosity, and formed of a self-expanding or balloon (or mechanical) expandable material including metallic or polymeric materials, to facilitate expansion of the outer stent. In FIG. 20A, outer stent 870 is the same length as inner stent 872. In the embodiment of FIGS. 20B and 20C, the outer stent 885 has a longer length and extends beyond both the proximal and distal ends of inner stent 887. In the embodiment of FIGS. 20D and 20E, the outer stent 888 has a longer length and extends beyond only one end (the proximal or distal end) of inner stent 889. In alternate embodiments, the inner stent can have a longer length than the outer stent such that it extends beyond one or both ends of the outer stent. In these embodiments, the woven layer, being the outermost layer abuts the vessel wall. The inner layer helps the stent expand more easily as it moves from a collapsed condition to an expanded condition as braided stents are "lazy" and sometimes reluctant to expand once crimped. Also, more porous stents are generally more efficient at expanding than lower porosity stents, such as low porosity woven stents.

In the embodiments of FIGS. 17A-20C, the less porous layer is flow diverting and has less pores to touch the endothelium so there is less likelihood of endoleaks, e.g., endoleak into the aneurysm. For example, by changing the flow dynamics by reducing the porosity, it causes the aneurysm to shrink over time.

In some embodiments, the more porous stent can have a porosity of over 50% and preferably over 80%. The less porous stent can have a porosity between 0% to about 80%, and in some embodiments between about 40% and 75%, depending on the porosity of the more porous stent, i.e., the % porosity of less porous stent is less than the % porosity of the more porous stent. Other porosity percentages are also contemplated.

The covered stents of the present invention are preferably delivered and deployed using a catheter or sheath (not shown). The covered stents can be deployed either out a distal end hole or a side hole formed in the microcatheter or sheath. The covered stents of the present invention can be either self-expanding so they expand when exposed from the delivery device or mechanically expanded such as expanded by a pull wire or an expandable structure within the stent or expanded by inflation of a balloon positioned within the stent and mounted on the catheter, and/or combinations thereof.

In the covered stents of the present invention, as discussed above, the covers (capes) cape could be attached to the stent body either at or adjacent the distal end of the stent body or at or adjacent the proximal end of the stent body, or at other regions, including for example medial regions, along the stent body. When the stent is deployed/expanded using a balloon then in preferred embodiments the cover is attached toward the proximal end of the stent body because the balloon pushes expands/opens the stent. When stent is deployed using a wire (not shown), then in preferred embodiments the cover is attached toward the distal end of the stent body because the wire is pulled in a proximal direction. Nonetheless, alternate configurations are envisioned with each type of expansion.

As discussed above, the shingling effect can be achieved with covers of various geometric shapes that are not necessarily circumferential around the entire stent. Non-limiting examples include multiple triangles, wherein the covered segment has shingling that will effectively entirely cover the "covered" zone. Again, the shingled coverings can be disposed upon the inner surface or outer surface or both the inner surface and outer surface of the stent body.

As discussed above, the covers of the present invention can be on the outside or inside of the stent body, attached to an outer wall/outer structure or an inner wall/inner structure of the stent body. In some embodiments, one or more of the covers can be attached on the outside while one or more of the other covers can be attached on the inside. In some embodiments, the attachment is on the distal end (spanning a punctate/very short distance) of the covered zone. The covering can cover anywhere from about 0.1% to 100% of the stent body. In some embodiments, it covers the central or medial portion of the stent body (skeleton) while leaving the distal and proximal regions uncovered; in other embodiments it covers the distal region leaving the proximal region uncovered and in other embodiments it covers the proximal region leaving the distal region uncovered. In some embodiments, the attachment zone is circumferentially around the stent in a distal region which can make delivery easier. However, it can alternatively be at a proximal region as well as discussed above. If attached at a medial region, it can be attached so there are two unattached free ends at each end of the stent.

The covered stents of the present invention with free unattached ends results in covered stents which can more freely bend along the contour of tortuous vessels, without kinking or straightening the vessel, compared to prior stents that have multiple or diffuse attachments between the cover and the stent body (skeleton). This also increases the tortuosity of the anatomy of vessels within which these covered stents can be safely and effectively delivered and deployed. The outer end of any curve requires a larger radius than the inner curve and the diffuse attachments of a typical covered stent require a fixed amount of the cover, e.g., fabric, per interstices or zone of the stent, thus making the stent much stiffer.

The covers of the present invention could be in the form of a "fabric" such as nylon, Dacron, pericardium, polyester, PET, PTFE or any other nonporous or minimally porous material, wherein the fabric is only attached on one side, such as the distal end of the fabric or the proximal end of the fabric, to the stent body. The attachment zone can be from as small as a punctate point circumferentially around the stent, to as much as 98%, provided there is a sufficient free end region to reduce stiffness as discussed above. In preferred embodiments, the attachment point would be very short. In preferred embodiments, the "fabric" layer is outside the "frame/skeleton" layer, however alternatively it could be inside. When attached on the outside (exterior surface of the stent body), it will contact the vessel walls upon deployment and full stent expansion to the circumference of the vessel; when, attached on the interior surface such that it is disposed within the stent skeleton, the skeletal outer surface will abut the vessel wall.

The skeleton is a separate component to which the one or more covers are attached. Preferably, the cover is composed of a different material than the stent body. The "skeletons" of the present invention can be composed of semi-rigid but flexible materials, such as metal alloys (containing chromium cobalt, and/or platinum, and/or nickel, titanium, steel, etc.) or synthetic fibers such as vicryl. The covers are preferably attached to the stent body in manufacture so the covered stents are inserted into the body and placed in position with the covers attached to the stent body.

The stent covers can expand independently of each other and/or independently of the stent body except at the attachment site.

Each of the embodiments disclosed herein can optionally have at least one uncovered opening in the covered stent.

Each of the embodiments disclosed herein can optionally have multiple covered zones and can optionally have multiple uncovered zones.

Elements of the covered stents of the present invention may be biodegradable or nondegradable. Alternatively, elements may be composed of both biodegradable and nondegradable elements. An element can be complete components of a particular part of the covered stents of the present invention or sub-components of each part.

The covered stents may optionally contain radiopaque components and/or radiopaque markers. These can be especially beneficial at ends of the stent and at the ends of the covered zone. Radio-opaque materials and markers can also be provided in other regions of the covered stent, and in some embodiments can be provided throughout the covered stent.

In some embodiments, the overlapping and/or shingled covers, (e.g., fabric layers) may have an additional "frame/skeleton" lattice supporting it, wherein that skeleton/frame is primarily supporting that "fabric" layer, and is an independent (but attached) skeleton layer to the main skeleton cylinder of the stent. For example, if there are triangular shingles of fabric attached on one end of the triangles to the outside of a main metal skeleton/cylinder, each triangle of fabric may optionally have additional metal struts supporting it, wherein such skeleton is primarily free from the main cylinder (e.g., no more than 70% of the support skeleton for the unattached portion of the fabric is attached to the main skeleton cylinder).

In some embodiments, the stent skeleton is semi-cylindrical, having a discontinuous diameter and longitudinal edges overlapping in a loose coil in an undeployed state. The stent unrolls into an overlapping but substantially cylindrical or semi-cylindrical shape as the skeleton expands when inserted in a target vessel. In such stent configurations, the capes (covers) can be attached longitudinally.

The covered stents of the present invention may have branched stent elements. The stents can be fully re-sheathable or partly re-sheathable. The stent elements of the present invention may optionally be detachable.

It should be noted that in one representative example of a skeleton (stent body) and cover/fabric layer, which are attached in the manufacturing process, the fabric layer has an attachment length (relative to fabric) that can be as small as 0.00001% and as much as 98%, provided a sufficient free end is formed. In these embodiments, the fabric is attached at a location such that it covers a percentage of the skeletal surface. Relatively small attachment zones are present in preferred embodiments.

The degree of overlap of the stent covers can vary depending upon the diameter of the expanded stent skeleton and the lumen within which it is deployed.

It will be understood by those skilled in the art that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

Although the invention has been described in detail in the foregoing embodiments for the purpose of illustration, it is to be understood that such detail is solely for that purpose, and that variations can be made therein by those skilled in the art without departing from the spirit and scope of the invention.

Although the apparatus and methods of the subject invention have been described with respect to preferred embodiments, which constitute non-limiting examples, those skilled in the art will readily appreciate that changes and modifications may be made thereto without departing from the spirit and scope of the present invention as defined by the appended claims.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the present invention, terms such as "approximately," "about", "generally," "substantially," and the like should be understood to allow for variations in any numerical range or concept with which they are associated. It is intended that the use of terms such as "approximately", "about", "substantially", and "generally" should be understood to encompass variations on the order of 25%, or to allow for manufacturing tolerances and/or deviations in design.

The recitation of numerical ranges by endpoints includes all numbers within the range.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present invention.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A method of treating a vessel of a patient comprising:
   deploying a first stent across an opening in a vessel; and
   subsequently inserting within the first stent, a second stent including:

a frame;
a first cover configured such that the first cover extends across the opening in the vessel, the first cover having a first end attached to the frame and a second free end unattached to the frame; and
a second cover having an attached end and a free end, the free end of the first cover overlying the attached end of the second cover,
wherein insertion of the second stent within the first stent pins the first cover and the second cover between the first stent and the second stent.

2. The method according to claim 1, wherein the first stent is composed of a woven material and the second stent is composed of an expandable material and movable from a collapsed condition to an expanded condition to facilitate expansion of the first stent within the second stent.

3. The method according to claim 1, wherein the second stent is composed of a non-woven material.

4. The method according to claim 1, wherein the first cover is attached to an outer wall of the second stent.

5. The method according to claim 1, wherein the second stent is composed of a woven material.

6. The method according to claim 1, wherein a porosity of the second stent is greater than a porosity of the first stent.

7. The method according to claim 6, wherein the second stent has a porosity of greater than about 80%.

8. The method according to claim 1, wherein the first and second stents are delivered through an end hole in a delivery catheter.

9. The method according to claim 1, wherein the first stent is composed of a first material and the second stent is composed of a second different material.

10. The method according to claim 1, further comprising hydrogel adhered to one or more of the first stent, second stent or first cover, the hydrogel swellable to fill a gap in the first cover.

11. The method according to claim 1, wherein treating the vessel includes preventing an endoleak.

12. The method according to claim 1, wherein inserting the second stent includes inserting the second stent with the frame extending continuously between a proximal end and a distal end of the second stent.

13. A method of treating a vessel of a patient comprising:
deploying a first stent across an opening in a vessel; and
subsequently inserting a second stent within the first stent,
wherein the second stent includes:
a frame;
a first cover having a first end attached to the frame and a second free end unattached to the frame, the first cover configured to extend across the opening in the vessel, the first cover being impermeable to blood; and
a second cover having an attached end and a free end, the free end of the first cover overlying the attached end of the second cover,
wherein insertion of the second stent within the first stent pins the first cover and the second cover between the first stent and the second stent.

14. The method according to claim 13, wherein a porosity of the second stent is greater than a porosity of the first stent.

15. The method according to claim 13, wherein the first stent is composed of a first material and the second stent is composed of a second different material.

16. The method according to claim 13, further comprising hydrogel adhered to one or more of the first stent, second stent or first cover, the hydrogel swellable to fill a gap in the first cover.

17. The method according to claim 13, wherein inserting the second stent includes inserting the second stent with the frame extending continuously between a proximal end and a distal end of the second stent.

18. The method according to claim 13, wherein the second cover is impermeable to blood.

19. The method of claim 13, wherein treating the vessel includes preventing an endoleak.

20. The method of claim 13, wherein the second stent further comprises a third cover.

* * * * *